US009029596B2

(12) United States Patent
Yoshida et al.

(10) Patent No.: US 9,029,596 B2
(45) Date of Patent: May 12, 2015

(54) METHODS FOR PRODUCING ACRYLIC ACID AND/OR ESTER THEREOF AND POLYMER OF THE ACRYLIC ACID AND/OR ESTER THEREOF

(75) Inventors: Hiroshi Yoshida, Osaka (JP); Hisashi Kamei, Osaka (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 13/997,350

(22) PCT Filed: Dec. 28, 2011

(86) PCT No.: PCT/JP2011/080461
§ 371 (c)(1),
(2), (4) Date: Jun. 24, 2013

(87) PCT Pub. No.: WO2012/091114
PCT Pub. Date: Jul. 5, 2012

(65) Prior Publication Data
US 2013/0281649 A1    Oct. 24, 2013

(30) Foreign Application Priority Data

Dec. 28, 2010  (JP) ................. 2010-291957
Jul. 22, 2011  (JP) ................. 2011-160923

(51) Int. Cl.
| | | |
|---|---|---|
| C07C 53/00 | (2006.01) |
| C07C 51/377 | (2006.01) |
| C07C 51/347 | (2006.01) |
| C07C 51/44 | (2006.01) |
| C08F 2/00 | (2006.01) |
| C08F 120/06 | (2006.01) |
| C12P 7/42 | (2006.01) |

(52) U.S. Cl.
CPC ............ *C07C 51/377* (2013.01); *C07C 51/347* (2013.01); *C07C 51/44* (2013.01); *C08F 2/00* (2013.01); *C12P 7/42* (2013.01); *C08F 120/06* (2013.01)

(58) Field of Classification Search
CPC .... C07C 51/44; C07C 51/347; C07C 51/377; C07C 57/04; C07C 59/01; C08F 120/06; C08F 2/00; C12P 7/42; C12P 7/62
USPC ........................................ 526/317.1; 562/599
See application file for complete search history.

(56) References Cited

U.S. PATENT DOCUMENTS

| | | | |
|---|---|---|---|
| 2,469,701 A | 5/1949 | Redmon et al. | |
| 2,859,240 A | 11/1958 | Holmen et al. | |
| 4,729,978 A | 3/1988 | Sawicki | |
| 4,786,756 A | 11/1988 | Paparizos et al. | |
| 5,068,399 A | 11/1991 | Naito et al. | |
| 5,250,729 A | 10/1993 | Abe et al. | |
| 6,388,000 B1 | 5/2002 | Irie et al. | |
| 7,538,247 B2 * | 5/2009 | Craciun et al. ................ 564/141 |
| 2006/0036043 A1 * | 2/2006 | Nestler et al. ............... 525/329.7 |
| 2007/0219391 A1 | 9/2007 | Lilga et al. | |
| 2007/0219521 A1 | 9/2007 | Hird et al. | |
| 2008/0119626 A1 | 5/2008 | Fujimaru et al. | |
| 2009/0023006 A1 | 1/2009 | Bub et al. | |
| 2009/0076297 A1 | 3/2009 | Bogan, Jr. et al. | |
| 2009/0325248 A1 * | 12/2009 | Marx et al. ..................... 435/141 |
| 2010/0190222 A1 * | 7/2010 | Ito et al. ........................ 435/139 |
| 2011/0105791 A1 * | 5/2011 | Kuppinger et al. ........... 562/599 |
| 2011/0139659 A1 | 6/2011 | Hird et al. | |
| 2012/0277467 A1 | 11/2012 | Onda et al. | |
| 2013/0157328 A1 | 6/2013 | Ozmeral et al. | |

FOREIGN PATENT DOCUMENTS

| | | | |
|---|---|---|---|
| EP | 0942014 A2 * | 9/1999 |
| GB | 751750 | 7/1956 |
| GB | 1 359 353 | 7/1974 |
| JP | 2-196753 | 8/1990 |
| JP | 3-167157 | 7/1991 |
| JP | 6-122707 | 5/1994 |
| JP | 2000-264859 | 9/2000 |
| JP | 2005-521718 | 7/2005 |
| JP | 2008-534695 | 8/2008 |
| JP | 2010-501526 | 1/2010 |
| JP | 2010-180171 | 8/2010 |
| WO | 02/090312 | 11/2002 |
| WO | 03/082795 | 10/2003 |
| WO | WO2004/076398 | * 9/2004 |

(Continued)

OTHER PUBLICATIONS

International Search Report issued Apr. 3, 2012 in International (PCT) Application No. PCT/JP2011/080461.

Shi et al., "KNaY-zeolite catalyzed dehydration of methyl lactate", Chinese Chemical Letters, vol. 18, 2007, pp. 476-4783.

Zhang et al., "Evaluation of Catalysts and Optimization of Reaction Conditions for the Dehydration of Methyl Lactate to Acrylates", Chinese Journal of Chemical Engineering, vol. 16, No. 2, 2008, pp. 263-269.

Zhang et al., "Catalytic Dehydration of Lactic Acid to Acrylic Acid Over Sulfate Catalysts", The Canadian Journal of Chemical Engineering, vol. 86, Dec. 2008, pp. 1047-1053.

(Continued)

*Primary Examiner* — Yevegeny Valenrod
*Assistant Examiner* — Blaine G Doletski
(74) *Attorney, Agent, or Firm* — Wenderoth, Lind & Ponack, L.L.P.

(57) ABSTRACT

A method for producing acrylic acid and/or an ester thereof from a raw material composition containing hydroxypropionic acid and/or an ester thereof, the method including the steps of: (a) evaporating the raw material composition; and (b) dehydrating the evaporated raw material composition by contact with a dehydration catalyst, wherein the total amount of hydroxypropionic acid and/or an ester thereof supplied in the step (b) is controlled to be 70% by mass or more based on 100% by mass of the total amount of hydroxypropionic acid and/or an ester thereof supplied in the step (a).

14 Claims, 2 Drawing Sheets

(56) References Cited

FOREIGN PATENT DOCUMENTS

| WO | 2005/095320 | 10/2005 |
|---|---|---|
| WO | 2006/092271 | 9/2006 |
| WO | 2007/042494 | 4/2007 |
| WO | 2007/106099 | 9/2007 |
| WO | 2007/106100 | 9/2007 |
| WO | 2008/042958 | 4/2008 |

OTHER PUBLICATIONS

Lee et al., "Efficient dehydration of methyl lactate to acrylic acid using $Ca_3(PO_4)_2$—$SiO_2$ catalyst", Catalysis Communications, vol. 11, 2010, pp. 1176-1180.

Xu et al., "Advances in the Research and Development of Acrylic Acid Production from Biomass", Chinese Journal of Chemical Engineering, vol. 14, No. 4, 2006, pp. 419-427.

Yan et al., "NaY zeolites modified by $La^{3+}$ and $Ba^{2+}$: the effect of synthesis details on surface structure and catalytic performance for lactic acid to acrylic acid", Journal of Rare Earths, vol. 28, No. 5, Oct. 2010, pp. 803-806.

Wang et al., "Rare earth metal modified NaY: Structure and catalytic performance for lactic acid dehydration to acrylic acid", Catalysis Communications, vol. 9, 2008, pp. 1799-1803.

Sun et al., "NaY Zeolites Catalyze Dehydration of Lactic Acid to Acrylic Acid: Studies on the Effects of Anions in Potassium Salts", Ind. Eng. Chem. Res., vol. 49, 2010, pp. 9082-9087.

Zhang et al., "Efficient Acrylic Acid Production through Bio Lactic Acid Dehydration over NaY Zeolite Modified by Alkali Phosphates", ACS Catalysis, vol. 1, 2011, pp. 32-41.

Gunter et al., "Catalysts and Supports for Conversion of Lactic Acid to Acrylic Acid and 2,3-Pentanedione", Ind. Eng. Chem. Res., vol. 34, 1995, pp. 974-980.

Wadley et al., "Lactic Acid Conversion to 2,3-Pentanedione and Acrylic Acid over Silica-Supported Sodium Nitrate: Reaction Optimization and Identification of Sodium Lactate as the Active Catalyst", Journal of Catalysis, vol. 165, 1997, pp. 162-171.

Fan et al., "Selective Catalysis of Lactic Acid to Produce Commodity Chemicals", Catalysis Reviews, vol. 51, 2009, pp. 293-324.

Shi et al., "KNaY-zeolite catalyzed dehydration of methyl lactate", Chinese Chemical Letters, vol. 18, 2007, pp. 476-478.

* cited by examiner

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial Sequence
<220> FEATURE:
<223> OTHER INFORMATION: Forward primer

<400> SEQUENCE: 1
gcgcgccata tgttaattcg cctgaccggc c                              31

<210> SEQ ID NO 2
<211> LENGTH: 32
<212> TYPE: DNA
<213> ORGANISM: Artificial Sequence
<220> FEATURE:
<223> OTHER INFORMATION: Reverse primer

<400> SEQUENCE: 2
gcgcgcagat cttcagtttc tctcacttaa cg                             32

<210> SEQ ID NO 3
<211> LENGTH: 24
<212> TYPE: DNA
<213> ORGANISM: Artificial Sequence
<220> FEATURE:
```

```
<223> OTHER INFORMATION: Forward primer

<400> SEQUENCE: 3
gaaggagata tacatatggc gcgc                                              24

<210> SEQ ID NO 4
<211> LENGTH: 26
<212> TYPE: DNA
<213> ORGANISM: Artificial Sequence
<220> FEATURE:
<223> OTHER INFORMATION: Reverse primer

<400> SEQUENCE: 4
ccgatatcca attgagatct gcgcgc                                            26

<210> SEQ ID NO 5
<211> LENGTH: 36
<212> TYPE: DNA
<213> ORGANISM: Artificial Sequence
<220> FEATURE:
<223> OTHER INFORMATION: Forward primer

<400> SEQUENCE: 5 gggggggccat atgaattttc atcatctggc ttactg                                36

<210> SEQ ID NO 6
<211> LENGTH: 35
<212> TYPE: DNA
<213> ORGANISM: Artificial Sequence
<220> FEATURE:
<223> OTHER INFORMATION: Reverse primer

<400> SEQUENCE: 6
ccccagatct tcaggcctcc aggcttatcc agatg                                  35

<210> SEQ ID NO 7
<211> LENGTH: 65
<212> TYPE: DNA
<213> ORGANISM: Artificial Sequence
<220> FEATURE:
<223> OTHER INFORMATION: Forward primer

<400> SEQUENCE: 7
cccccccata tgtgtttcct gtgtgaaatt gttatccgct cacaattcca cacaatatac      60
gagcc                                                                   65

<210> SEQ ID NO 8
<211> LENGTH: 43
<212> TYPE: DNA
<213> ORGANISM: Artificial Sequence
<220> FEATURE:
<223> OTHER INFORMATION: Reverse primer

<400> SEQUENCE: 8
ccccggatcc ttagttaagc cagccccgac acccgccaac acc                         43
```

METHODS FOR PRODUCING ACRYLIC ACID AND/OR ESTER THEREOF AND POLYMER OF THE ACRYLIC ACID AND/OR ESTER THEREOF

TECHNICAL FIELD

The present invention relates to a method for producing acrylic acid and/or an ester thereof from hydroxypropionic acid and/or an ester thereof, and a method for producing a hydrophilic resin.

BACKGROUND ART

Acrylic acid is widely used on an industrial scale as a raw material of water-absorbent resins and the like, and is commonly produced by two-step oxidation in a fixed bed multitubular continuous reactor. In the two-step oxidation, propylene is converted to acrolein by catalytic gas-phase oxidation in the presence of an oxide catalyst, and the resulting acrolein is subjected to catalytic gas-phase oxidation to produce acrylic acid. Since propylene is a raw material derived from fossil resources, production of acrylic acid from renewable resources is desired.

Additionally, an acrylic ester is produced by esterification of acrylic acid to be widely used as a raw material of various resins such as adhesives and coating compositions.

An attempt has been made for economically producing acrylic acid on a commercial scale from biomass that is a renewable resource. Examples of a method for producing acrylic acid from biomass include a method dehydrating hydroxypropionic acid (also referred to as HP) to prepare acrylic acid. Examples of hydroxypropionic acid include such as lactic acid (also referred to as 2-hydroxypropionic acid or 2HP) that is a natural product and is easily available and 3-hydroxypropionic acid (also referred to as 3HP) prepared by fermenting sugars obtained from natural products or obtained by decomposition of cellulose.

Patent Literature 1 discloses a method in which an aqueous or other solution containing β-hydroxycarboxylic acid or its salt obtained by fermentation or the like is prepared, and the solution is heated in the presence or absence of a dehydration catalyst for dehydration, thereby producing unsaturated carboxylic acid or its salt.

Patent Literature 2 discloses a method in which an aqueous solution containing α- or β-hydroxycarboxylic acid is introduced to a site retaining an inactive ceramic and the like or an acidic solid catalyst, and heated to prepare α, β-unsaturated carboxylic acid. Though Patent Literature 2 further teaches that an aqueous solution containing a polymer, oligomer, lactide, lactone, or the like produced from α- or β-hydroxycarboxylic acid may be used, no specific examples are mentioned.

In the case where acrylic acid is produced by vapor phase dehydration in which a raw material composition containing hydroxypropionic acid is evaporated and brought into contact with a catalyst, an accretion may be formed in an evaporator or reactor eventually to block the evaporator or reactor, problematically resulting in a failure in stable production for a long time. In addition, the catalyst surface covered with the accretion lowers the catalytic activity, problematically leading to lowering in the conversion of hydroxypropionic acid. As a result, the produced acrylic acid may contain unconverted hydroxypropionic acid. In such a case, problematically, the purity of the acrylic acid may be lowered or the hydroxypropionic acid may react with the acrylic acid to lower the yield of the acrylic acid in purification step after the reaction.

A hydrophilic resin, in particular, a water-absorbent resin is demanded to have a reduced residual monomer content from the viewpoint of its performance and safety. Accordingly an acrylic acid raw material used in preparation of water-absorbent resin is strongly demanded to have fewer impurities such as hydroxypropionic acid, dimers, and oligomers which may cause residual monomers in the water-absorbent resin (Patent Literature 3, Patent Literature 4). In the above methods, however, the resulting acrylic acid contains a large amount of unreacted hydroxypropionic acid monomers and heavy byproducts, and therefore, complicated purification needs to be performed. Consequently, the above methods are technically insufficient for obtaining acrylic acid to be used as a raw material of a water-absorbent resin and have room for improvement.

CITATION LIST

Patent Literature

Patent Literature 1: JP-T 2005-521718
Patent Literature 2: WO 2005/095320
Patent Literature 3: JP-A 06-122707
Patent Literature 4: JP-T 2008-534695

SUMMARY OF INVENTION

Technical Problem

The present invention aims to provide a method for stably producing highly pure acrylic acid for a long time by a gas phase reaction using hydroxypropionic acid as a raw material, without causing a blockage in an evaporator or reactor and without lowering the conversion of hydroxypropionic acid, while reducing the amount of byproducts such as heavy substances formed in a side reaction. In addition, the present invention also aims to provide a method for producing a water-absorbent resin with excellent performance and high safety using acrylic acid containing fewer impurities as a raw material.

Solution to Problem

The present inventors have intensively studied to accomplish the above aims and have found the following solution. In production of acrylic acid and/or an ester thereof from a raw material composition containing hydroxypropionic acid and/or an ester thereof, a production method includes the steps of evaporating the raw material composition and dehydrating the evaporated raw material composition by contact with a dehydration catalyst to synthesis(c) acrylic acid and/or an ester thereof in the dehydration reaction. The production of acrylic acid and/or an ester thereof is carried out under the condition that the total amount of hydroxypropionic acid and/or an ester thereof supplied in the dehydration step is controlled to be 70% by mass or more based on the 100% by mass of the total amount of hydroxypropionic acid and/or an ester thereof supplied in the evaporation step, thereby suppressing a blockage in an evaporator or reactor ox reduction, in the conversion of hydroxypropionic acid and/or an ester thereof caused by lowered catalytic activity. Accordingly, stable production of highly pure acrylic acid and/or an ester thereof for a long time is achieved. In this manner, the present invention has been completed.

Specifically, the present invention includes the following aspects.

(1) A method for producing acrylic acid and/or an aster thereof from a raw material composition containing hydroxypropionic acid and/or an ester thereof, the method including the steps of; (a) evaporating the raw material composition; and (b) dehydrating the evaporated raw material composition by contact with a dehydration catalyst, wherein the total amount of hydroxypropionic acid and/or an ester thereof supplied in the step (b) is controlled to be 70% by mass or more based on 100% by mass of the total amount of hydroxypropionic acid and/or an ester thereof supplied in the step (a).

(2) The production method according to (1), wherein at least part or ail of the hydroxypropionic acid in the raw material composition is hydroxypropionic acid obtainable by fermentation.

(3) The production method according to (1) or (2), wherein an inorganic compound in the raw material composition is 1% by mass or less based on 100% by mass of the total amount of the hydroxypropionic acid and/or an ester thereof.

(4) The production method according to any one of (1) to (3), wherein the total amount of water and/or an inert gas supplied in the step (a) is 0.5 times by mole or more of the total amount of the hydroxypropionic acid and/or an ester thereof in the raw material composition.

(5) The production method according to any one of (1) to (4), wherein the hydroxypropionic acid is 3-hydroxypropionic acid.

(6) The production method according to any one of (1) to (5), wherein a carbonaceous substance formed on the dehydration catalyst in the step (b) is removed by contact with an oxidant.

(7) The production method according to (6), wherein the oxidant is a gaseous oxidant.

(8) The production method according to (7), wherein the carbonaceous substance is removed by introducing the gaseous oxidant into a reactor filled with the dehydration catalyst used in the step (b).

(9) The production method according to any one of (6) to (8), wherein the method includes the steps of: a first hydroxypropionic acid reaction step including the step (a) and the step (b); catalyst regeneration step for removing the carbonaceous substance on the dehydration catalyst; and a second hydroxypropionic acid reaction step including the step (a) and the step (b) in which the dehydration catalyst regenerated in the catalyst regeneration step is used.

(10) The production method according to (9), wherein plural reactors are used in production of acrylic acid and/or an ester thereof, and, while the catalyst regeneration step is performed in a first reactor, the first or second hydroxypropionic acid reaction step is performed in a second reactor.

(11) The production method according to (9) or (10), wherein the method further includes a step of removing a carbonaceous substance formed in an evaporator in the step (a) by contact with an oxidant.

(12) The production method according to any one of (1) to (11), wherein the method further includes a step of purifying acrylic acid and/or an ester thereof by crystallization.

(13) A method for producing a hydrophilic resin comprising a step of polymerizing a monomer component containing acrylic acid and/or an ester thereof produced by the production method according to any one of (1) to (12).

(14) The method for producing a hydrophilic resin according to (13), wherein the hydrophilic resin is a water-absorbent resin.

Advantageous Effects of Invention

The present invention provides a method for producing acrylic acid and/or an ester thereof, in which a blockage in an evaporator or reactor and lowering of the catalytic activity are suppressed and hydroxypropionic acid and/or an ester thereof is efficiently converted so that the acrylic acid and/or an ester thereof is stably produced for a long time. With this production method, acrylic acid and/or an ester thereof can be stably and continuously produced in high yield. In addition, use of the acrylic acid and/or an ester thereof prepared by the production method of the present invention in production of a hydrophilic resin can lower the residual monomer content in the hydrophilic resin.

DESCRIPTION OF EMBODIMENTS

Figure 1:
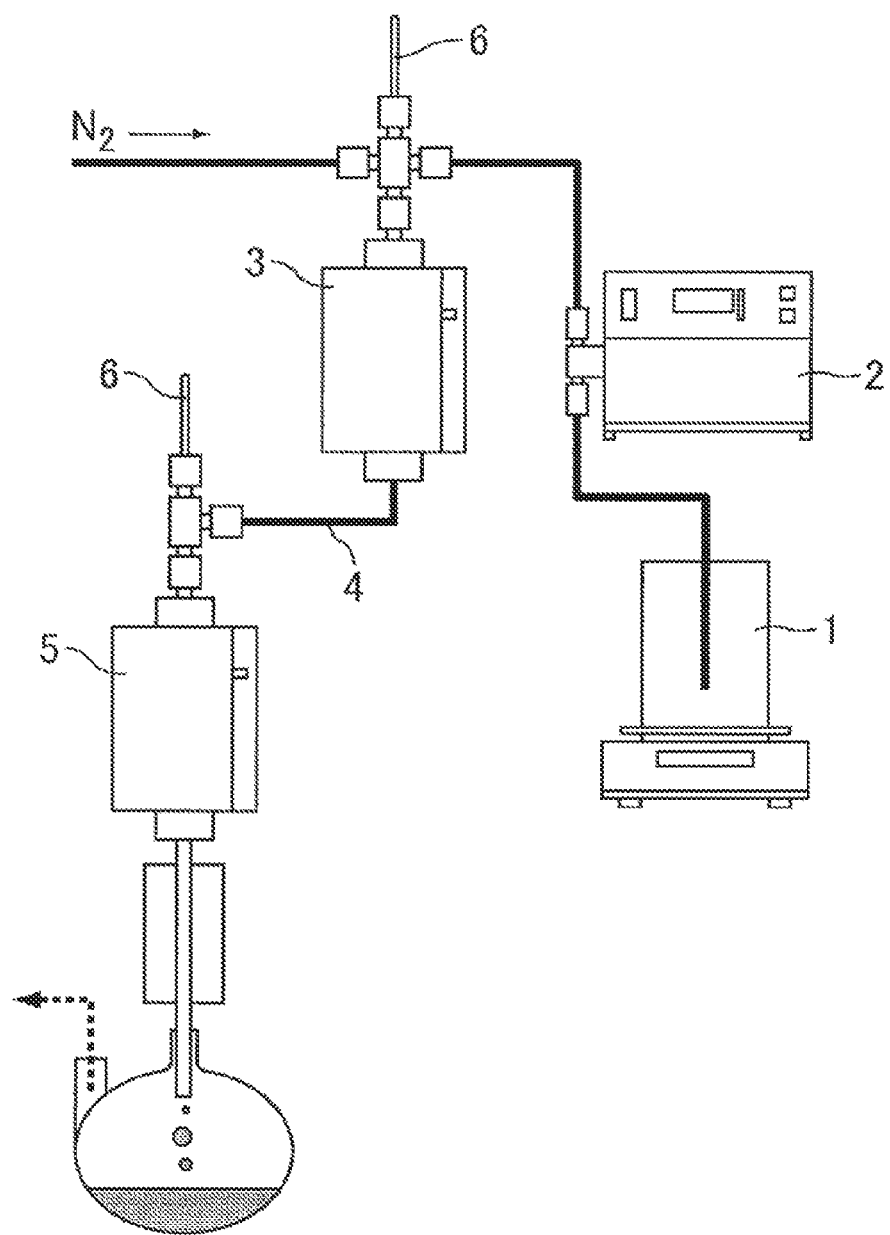
FIG. 1 is a schematic diagram illustrating one example of a preferable embodiment of evaporation step and dehydration step.

The following will discuss the present invention in detail.
It is to be noted that a combination of two or more preferable embodiments of the present invention described below is also a preferable embodiment of the present invention.

<Method for Producing Acrylic Acid and/or an Ester Thereof>

The present invention relates to a method for producing acrylic acid and/or an ester thereof from a raw material composition containing hydroxypropionic acid and/or an ester thereof (also simply referred to as a raw material composition). The method includes the steps of (a) evaporating the raw material composition and (b) dehydrating the evaporated raw material composition by contact with a dehydration catalyst. The total amount of hydroxypropionic acid and/or an ester thereof supplied in the step (b) is controlled to be 70% by mass or more based on the 1001 by mass of the total amount of hydroxypropionic acid and/or an ester thereof supplied in the step (a).

In the present description, the "hydroxypropionic acid and/or an ester thereof" herein is represented by hydroxypropionic acid, unless otherwise specified. The "acrylic acid and/or an ester thereof" is represented by acrylic acid. A hydroxypropionic acid ester and an acrylic acid ester can be each prepared by esterification of the corresponding acid by a method described later.

In the present invention, hydroxypropionic acid is at least one compound selected from 2-hydroxypropionic acid and 3-hydroxypropionic acid. Preferred as hydroxypropionic acid is 3-hydroxypropionic acid.

The raw material composition containing hydroxypropionic acid essentially contains the hydroxypropionic acid, and may additionally contain ester dimers or ether dimers of hydroxypropionic acid. The raw material composition may further contain a solvent or byproducts formed in preparation of hydroxypropionic acid.

The concentration of the total amount of hydroxypropionic acid and or its ester in the raw material composition is preferably 5 to 95% by mass, more preferably 7 to 90% by mass, and still more preferably 10 to 90% by mass.

The raw material composition containing hydroxypropionic acid may further contain a solvent. The solvent is not particularly limited as long as it can dissolve hydroxypropionic acid therein. Examples thereof include water, alcohols, hydrocarbons, ethers, ketones, esters, amines, amides, and the like. Each of these may be used alone or in combination of two or more types. The solvent preferably has a lower boiling point than hydroxypropionic acid for facilitating evaporation. A preferred solvent is water.

When the raw material composition contains a solvent in the present invention, the concentration of the solvent based on 100% by mass of the raw material composition is preferably 5 to 95% by mass, more preferably 10 to 93% by mass, and still more preferably 10 to 90% by mass. With a concentration of the solvent of 5% by mass or more, the viscosity is lowered to improve the handleability of the raw material composition and an effect of promoting evaporation of the hydroxypropionic acid is expected. With a concentration of 95% by mass or less, calories required for evaporation is suppressed, contributing reduction in cost.

The raw material composition containing hydroxypropionic acid may contain components other than hydroxypropionic acid, such as byproducts formed in synthesis of hydroxypropionic acid by fermentation, and the like. Specific examples of the byproducts include such as formic acid, acetic acid, propionic acid, butyric acid, succinic acid, fumaric acid, pyruvic acid, glycolic acid, ethanol, amino acids, 1,3-propanediol, glycerin, hydroxypropionaldehyde, and alanine, which are possibly formed together with hydroxypropionic acid in fermentation.

Hydroxypropionic acid used in the present invention is obtainable from various sources. In consideration of global warming and environmental protection, preferably used as carbon sources are renewable bio-based resources. Hydroxypropionic acid is also synthesized by hydrolysis of hydroxypropionitrile or propiolactone. Further, a hydroxypropionic acid ester is known to be synthesized from ethylene oxide, alcohol, and carbon monoxide.

Specific examples of hydroxypropionic acid include: 2-hydroxypropionic acid prepared by decomposing carbohydrates seen as cellulose by a catalyst; and 2-hydroxypropionic acid and 3-hydroxypropionic acid prepared by fermentation of sugars obtained from such as crops or obtained by decomposition of cellulose and the like.

In the present invention, at least part or all of hydroxypropionic acid in the raw material composition is preferably hydroxypropionic acid obtained by fermentation.

The raw material of hydroxypropionic acid is preferably a bio-based resource soon as biomass.

Fermentation in the present invention refers to conversion of an organic substance by microbial action for formation of a compound different from the raw material organic substance.

2-Hydroxypropionic acid is obtainable by a known method such as a method disclosed in JP-A 2008-120796 in which a carbohydrate-containing raw material such as a cellulosic biomass raw material is heat-processed in a solvent containing a Lewis acid catalyst. 2-Hydroxypropionic acid is also obtainable by fermentation using *lactobacillus* as disclosed in Advances in Applied Microbiology (Vol. 42, pp. 45-95, 1996) or fermentation using fungus (*Rhizopus crysae*) as disclosed in Enzyme and Microbial Technology (Vol. 26, pp. 87-107, 2000).

3-Hydroxypropionic acid is also obtainable by a known method such as fermentation using glucose as a carbon source and *Escherichia coli* in which a beta-alanine aminotransferase gene derived from *Streptomyces griseus* ATCC21897 is introduced as disclosed in WO 2008/027742. 3-Hydroxypropionic acid is also obtainable by fermentation of glycerin as a carbon source using *Escherichia coli* in which glycerin dehydratase derived from *Klebsiella pneumoniae* and aldehyde oxidase derived from *Escherichia coli* is introduced as disclosed in WO 2001/016346.

The known references are mentioned to show exemplary methods for obtaining hydroxypropionic acid. Bacteria or recombinant bacteria used in fermentation are not particularly limited, and hydroxypropionic acid prepared by fermentation using creatures capable of forming hydroxypropionic acid may be used in the production method of the present invention. Hydroxypropionic acid prepared by contact of sugars as the raw material with the creatures, not by fermentation, can also be converted to acrylic acid by the production method of the present invention.

The contact of sugars with the creatures also includes a reaction using microorganisms or treatment products thereof in the presence of sugars used as a raw material. Examples of the treatment products include microorganisms treated with acetone, toluene, or the like, dead microorganisms, freeze-dried microorganisms, broken microorganisms, cell-free extracts obtained by breaking microorganisms, crude enzyme liquids and purified enzyme extracted from these cell-free extracts, and the like. Also usable is hydroxypropionic acid obtained by a reaction using microorganisms, the treatment products, enzymes, and the like fixed to a carrier by a common method.

In the method for obtaining hydroxypropionic acid by fermentation using bio-based resources according to a specific embodiment of the present invention, microorganisms, biological substances, and the like are preferably separated from an aqueous composition containing solids (especially, fine plant parts or cells and/or cell fragments), hydroxypropionic acid and microorganisms formed by fermentation, and the like. The separation may be carried oat by a known method to those skilled in the art for separating solids from a liquid composition, and is preferably carried out by precipitation, centrifugation, or filtration. The separation is most preferably carried out by filtration.

The treatment of separation of microorganisms and the like from an aqueous composition containing hydroxypropionic acid, microorganisms and the like may be carried out without any treatment on the microorganism. Alternatively, the treatment of separation may include sterilization of the microorganisms. The sterilization of microorganisms in the aqueous composition may be performed before, during, or after separation of the microorganisms. Examples of the sterilization include heat treatment (sterilization of microorganisms by heating) and high-energy irradiation (e.g., sterilization of microorganisms by UV irradiation), and heat treatment is preferably employed.

In the heat treatment, an aqueous composition containing hydroxypropionic acid, microorganisms, and the like is heated for preferably at least 60 seconds, more preferably at least 10 minutes, and still more preferably at least 30 minutes, at a temperature of preferably at least 100° C., more preferably at least 110° C., and still more preferably at least 120° C. The heat treatment is preferably carried out in a device (e.g. autoclave) known to those skilled in the art.

As a raw material composition containing hydroxypropionic acid used in the present invention, a raw material composition containing fewer impurities is preferable.

A known method may be employed for obtaining a raw material composition containing fewer impurities. Specific examples thereof include; a method in which crude hydroxypropionic acid obtained by fermentation is reacted with a calcium salt to precipitate hydroxypropionic acid calcium salt, and then the recovered salt is reacted with an acid such as sulfuric acid for purification of hydroxypropionic acid; and a method in which hydroxypropionic acid ammonium salt obtained by fermentation is chemically converted to hydroxypropionic acid by electrodialysis or cation exchange for purification; and the like.

To a hydroxypropionic acid ammonium salt aqueous solution obtained by fermentation, a water-immiscible amine solvent is added. Then, the mixture is heated for removal of ammonia, thereby giving a solution of hydroxypropionic acid in an amine. Water is added to the solution, and the resulting mixture is heated, so that an aqueous solution of hydroxypropionic acid is prepared.

Alternatively, purification can be performed by evaporation utilizing vapor pressure of hydroxypropionic acid. However, since hydroxypropionic acid has a low vapor pressure and a side reaction such as oligomerization is likely to proceed by heating, evaporation with less heat history such as thin-layer evaporation under reduced pressure is preferable.

Further, purified hydroxypropionic acid can also be obtained by esterifying hydroxypropionic acid with an alcohol, distilling the resulting hydroxypropionic acid ester for purification, and hydrolyzing the hydroxypropionic acid ester.

In the raw material composition used in the present invention, an inorganic compound that is a medium component used in fermentation step may be present. Examples of the inorganic compound include disodium hydrogen phosphate, sodium dihydrogen phosphate, dipotassium hydrogen phosphate, potassium dihydrogen phosphate, ammonium chloride, sodium chloride, potassium chloride, magnesium chloride, calcium chloride, iron chloride, magnesium sulfate, sodium sulfate, manganese sulfate, zinc sulfate, iron sulfate, copper sulfate, and ammonium acetate, and the like.

Presence of an inorganic compound in the raw material composition may cause deposition of the inorganic compound in an evaporator, resulting in a blockage or lowered evaporation efficiency. In addition, effect of the inorganic compound may denature hydroxypropionic acid in the evaporator into oligomers or other byproducts, leading to reduction in the acrylic acid yield. If the inorganic compound is attached to the catalyst, the catalytic activity and the acrylic acid selectivity may be lowered.

The total amount of the inorganic compound based on 100% by mass of the total amount of hydroxypropionic acid and/or an ester thereof in the raw material composition is preferably 1% by mass or less, more preferably 0.5% by mass or less, and still more preferably 0.1% by mass or less. When the amount of the inorganic compound is 1% by mass or less, a blockage caused by deposition in the evaporator and excessive conversion of hydroxypropionic acid are suppressed and a decrease in catalytic activity during dehydration is suppressed, enabling stable operation for a long time.

The method for producing hydroxypropionic acid and/or an ester thereof of the present invention includes the steps of: (a) evaporating a raw material composition; and (b) dehydrating the evaporated raw material composition by contact with a dehydration catalyst, wherein the total amount of hydroxypropionic acid and/or an ester thereof supplied in the step (b) is controlled to be 70% by mass or more based on 100% by mass of the total amount of hydroxypropionic acid and/or an ester thereof supplied in the step (a).

In the present invention, dehydration can be carried out stably for a long time, provided that conversion of hydroxypropionic acid and an ester thereof is suppressed in the evaporation step (a) and, at the stage where the raw material composition is supplied in the dehydration step (b), the total amount of hydroxypropionic acid and/or an ester thereof in the raw material is controlled to 70% by mass or more based on 100% by mass of the total amount of hydroxypropionic acid and/or an ester thereof supplied in the step (a).

In other words, the total amount of hydroxypropionic acid and/or an ester thereof supplied in the step (b) controlled to 70% by mass or more indicates that the con-version of hydroxypropionic acid and/or an ester thereof (in total) supplied in the step (a) is controlled to 30% by mass or less.

Specifically, the total amount of hydroxypropionic acid and/or an ester thereof at the stage where the raw material composition is supplied in the dehydration step (b) (e.g., beginning of the dehydration step) is preferably 75% by mass or more, more preferably 80% by mass or more, and still more preferably 85% by mass or more.

The total amount of hydroxypropionic acid and/or an ester thereof supplied in the step (b) is controlled to 70% by mass or more by adjusting various factors such as the type and shape of the evaporator, temperature inside the evaporator, constituents of the raw material composition, the amount of an inert gas to coexist, and SV (space velocity) described later.

The total amount of hydroxypropionic acid and/or an ester thereof supplied in the step (b) is measured by analyzing a liquid obtained by cooling the gas sampled when the stage is moved from the evaporation step (a) to the dehydration step (b) by liquid chromatography or the like.

Hydroxypropionic acid has hydroxy and carboxyl groups in a molecule and comparatively easily has an intermolecular condensation reaction by dehydration by heating to form oligomers. The oligomers once formed are denatured by further heating and attach to a reaction tube to cause a blockage. Oligomers formed on the catalyst may cover the catalyst surface to deteriorate the reaction results or may be eventually converted to carbonaceous substances by further heating to lower the catalytic activity.

Since hydroxypropionic acid has a high boiling point, heating to high temperatures is needed for evaporation thereof. The evaporation rate is therefore slow, and if hydroxypropionic acid in a liquid form is heated for a certain period of time, the hydroxypropionic acid is easily reacted to be converted to a heavy compound such as oligomers. Here, oligomerization is an equilibrium reaction. Since water concurrently formed is soon evaporated because of its low boiling point, oligomerization is further promoted.

In the evaporation step, hydroxypropionic acid in the raw material composition is partially converted. A part thereof is converted to acrylic acid, whereas another part thereof is converted to a heavy product such as oligomers. A high conversion of hydroxypropionic acid during the evaporation step possibly causes a blockage in the evaporator by a formed heavy compound and lowers the evaporation performance of the evaporator with a thermal conductivity lowered by the attached heavy compound. Contact of the formed heavy compound with a catalyst layer promotes coking of the catalyst to significantly lower the catalytic activity and accelerates formation of a heavy product to cause a blockage in the catalyst layer.

However, if conversion of hydroxypropionic acid during the evaporation step is suppressed and the total amount of hydroxypropionic acid and/or an ester thereof in the raw material composition at the beginning of the dehydration step is controlled to 70% by mass or more of the total amount of the hydroxypropionic acid and/or an ester thereof at the beginning of the evaporation step, formation of a heavy product is moderate and a reaction is not stopped by a blockage, coking or the like, enabling a stable reaction for a long time.

Furthermore, in the case of conversion of hydroxypropionic acid in an evaporator, the hydroxypropionic acid forms a lot of unnecessary components such as a heavy product, though it partially forms acrylic acid. The acrylic acid selectivity is found to be lower than that in the case where hydroxypropionic acid is converted on the catalyst. Accordingly, excessive conversion of hydroxypropionic acid in an evaporator leads to reduction in formation of acrylic acid at an exit of the reactor, resulting in lowered productivity of acrylic acid. Therefore, suppression of the conversion of hydroxypropionic acid in an evaporator is important in production of acrylic acid in high yield.

The raw material composition containing hydroxypropionic acid is evaporated by heating. The temperature in an evaporator is preferably 130 to 500° C., more preferably 170 to 450°0 C., still more preferably 200 to 400° C., particularly preferably 220 to 370° C., and most preferably 220 to 320° C. A temperature within a range of 150 to 500° C. allows rapid evaporation of the raw material composition and prevents a blockage in the evaporator or reactor due to a side reaction. With a temperature of higher than 500° C., conversion of hydroxypropionic acid is increased and energy required for heating is excessively increased. In addition, the composition may possibly have coking to cause a blockage by attachment of a carbonaceous deposit in the evaporator or reactor.

A lower pressure inside the evaporator is advantageous because evaporation of the raw material composition is facilitated. However, the pressure needs to be determined in consideration of the appropriate pressure inside the reactor used subsequently, cost of equipment and the like. The pressure inside the evaporator is preferably 10 to 1000 kPa, more preferably 30 to 300 kPa, and still more preferably 50 to 250 kPa.

In terms of the supply rate of the raw material composition to an evaporator, from a viewpoint of reaction inhibition and the like, the gas formed by evaporation of all of the raw material composition supplied to the evaporator and other gases (including water vapor and inert gas described later) in total has a SV (space velocity) of preferably 100 to 100000/hour, more preferably 200 to 50000/hour, and still more preferably 600 to 30000/hour. The SV is defined as a value obtained by dividing the gas volume flow (converted at 0° C., 101 kPa) calculated from constituents of the raw material composition and other gases by the volume of the evaporator. The SV can be adjusted by changing the supply rate of the raw material composition.

The evaporator preferably has a configuration that heat is efficiently transferred to the raw material composition supplied in the liquid form. Examples thereof include horizontal- or vertical-tube evaporators of natural circulation type and those of forced circulation type.

In another method for evaporation, a flow channel of the raw material composition in an evaporator is filled with packing that has a large surface area per unit packing volume. Examples thereof include random packing and structured packing such as Raschia ring, Beri saddle, spherical moldings, wire-mesh moldings (e.g. Dixon packing, McMahon packing), and Meliapak (manufactured by Sniper Chemtech Ltd.). The raw material composition is supplied to such an evaporator with a large surface area where the raw material composition (liquid) is to contact for evaporation. Accordingly, the supplied raw material composition is to contact the packing having a large surface area. In that case, the heating area increases to allow efficient heat transfer, allowing evaporation in a short time. As a result, the conversion of the raw material composition in the evaporator is lowered.

Exemplary materials of the packing include metallic materials such as iron and stainless steel, and inorganic materials such as silica and ceramics.

The surface area of the packing put in the evaporator is preferably 5 cm$^2$/cm$^3$ or more, more preferably 10 cm$^2$/cm$^3$ or more, still more preferably 20 cm$^2$/cm$^3$ or more, and particularly preferably 30 cm$^2$/cm$^3$ or more. The upper limit thereof is, though not particularly limited, preferably 1000 cm$^2$/cm$^3$ or less and more preferably 800 cm$^2$/cm$^3$ or less.

In still another method for evaporation, using a thin-film type heat exchanger of rising liquid film type, failing liquid film type, or agitated liquid film type, the surface area of the liquid is increased, allowing evaporation in a short time. In another method, the composition is dispersed in fine droplets for evaporation using a spray, atomizer, or the like. The size of droplets is preferably 1 mm or less and more preferably 0.5 mm or less.

For another example, a flash evaporator may be used in which a heated raw material composition is supplied to an evaporation chamber and evaporated. In the flash evaporator, the raw material composition can be heated to be liquidized under ordinary pressure or increased pressure, supplied to an evaporation chamber under reduced pressure or ordinary pressure, and evaporated.

Further, the raw material composition may be supplied to a fluidized-bed evaporator to be evaporated. For example, after fluidizing granulation of inert solids by an inert gas, the raw material composition may be supplied to a heated fluidized-bed evaporator to be evaporated.

The raw material composition also may be evaporated by the above methods in several steps. For example, an evaporator filled with packing may be arranged next to a flash evaporator, and the raw material composition is partially evaporated in the flash evaporator and the rest of the composition is evaporated in the evaporator filled with packing.

In evaporation of the raw material composition, the above methods also may be used in combination. For example, the raw material composition can be sprayed and evaporated in an evaporator filled with packing.

In a preferable embodiment of the evaporation step, evaporation is carried out together with introduction of other gases (including water vapor, inert gas and the like). Introduction of other gases containing water, inert gas, and the like together with the raw material composition is preferable because it promotes evaporation of hydroxypropionic acid to allow continuation of a stable reaction.

Examples of the other gases include such as nitrogen, helium, argon, carbon dioxide, and water vapor. Each of these may be used alone or used in combination of two or more types. Preferred are nitrogen and water vapor. The water vapor herein includes water vapor formed by evaporation of water contained in the raw material composition as a solvent.

With regard to the amount of other gases supplied, the total amount of water and/or inert gas is preferably 0.5 to 100 molar times and more preferably 1 to 50 molar times based on the total amount of hydroxycarboxylic acid and/or an ester thereof in the raw material composition.

Exemplary heating methods include: heating from outside the evaporator using beat sources such as steam, heat media, molten salt, and heaters (e.g., jacketed evaporator); and heating with use of a heat source provided inside the evaporator such as coils. For another example, heated water vapor or an inert gas such as nitrogen, argon, helium, and carbon dioxide is supplied to the evaporator to contact with the raw material composition for application of heat. These methods may be used in combination.

For a preferable example, the raw material composition is sprayed to the heated packing for evaporation. Further, heated nitrogen or water vapor may be concurrently supplied thereto.

Any reactor may be used in the dehydration step as long as it can hold a solid catalyst inside and be heated. Examples thereof include such as a fixed bed continuous reactor and a fluidized bed continuous reactor. Preferred is a fixed bed continuous reactor.

In the case of the fixed bed continuous reactor, a catalyst is placed therein and heated, and vapor of the raw material composition is supplied thereto. The flow of the raw material composition vapor may be an upward, downward, or horizontal flow. For easy heat exchange, a fixed bed multitubular continuous reactor is suitably used.

In the case of the fluidized bed continuous reactor, a granular catalyst is placed in the reactor and fluidized by vapor of the raw material composition or an inert gas separately supplied during the reaction. Since the catalyst fluidizes, a blockage by heavy substances is less likely to occur. Further, the catalyst may be partially taken out continuously and a new catalyst or regenerated catalyst may be continuously supplied.

The dehydration step is carried out after the evaporation step, and another step may be carried out between them. For example, vapor of the raw material composition evaporated in the evaporator may be subjected to a temperature control step for heating/cooling the vapor to a predetermined temperature before the dehydration step in the reactor.

In a preferable embodiment of the evaporation step and dehydration step, for example, vapor of the raw material composition evaporated in the evaporator is supplied to a reactor connected via a connecting pipe, and the like. FIG. 1 shows a schematic view of one example of this embodiment. In the drawing, the supply rate of the raw material composition is measured using a scale 1 and the raw material composition is supplied to an evaporator 3 using a pump 2 for evaporation. The evaporated raw material composition is supplied to a reactor 5 via a connecting pipe 4 so as to be reacted by contact with a dehydration catalyst, thereby producing acrylic acid and/or an ester thereof.

The evaporator and reactor may be integrated with each other. In a preferable embodiment, for example, the reaction tube is filled with packing having a large surface area as an evaporation layer and a catalyst is loaded under the evaporation layer, so that the evaporation step is performed at the evaporation layer and the dehydration step is performed at a catalyst layer.

In another preferable embodiment, a single or plural evaporation layers may be connected with a multitubular reactor filled with a catalyst.

In any of these cases, the total amount of the hydroxypropionic acid and/or an ester thereof supplied in the step (b) refers to the amount at the beginning of the step (b).

In the case where an evaporator is connected with a reactor via a connecting pipe as in the case of FIG. 1, gas from the evaporator is sampled using a sampling outlet provided in the connecting pipe 4, and analyzed for determination of the total amount of hydroxypropionic acid and/or an ester thereof at the beginning of the dehydration step.

In the case where an evaporation layer and a catalyst layer are stacked (integrated), gas from the evaporation layer is sampled using a sampling outlet provided between the evaporation layer and the catalyst layer, and analyzed for determination of the total amount of hydroxypropionic acid and/or an ester thereof at the beginning of the dehydration step. For another example, an operation is performed only at an evaporation layer and conditions are adjusted such that the total amount of hydroxypropionic acid and/or an ester thereof in the resulting gas is 70% by mass or more based on the total amount of the supplied hydroxypropionic acid and/or an ester thereof. Then, a catalyst is loaded and the reaction is carried out.

In the case where one or plural evaporation layers are connected with a multitubular reactor containing a catalyst, gas from the last evaporation layer is sampled from a sampling outlet provided between the last evaporation layer and the first reactor, and analyzed for determination of the total amount of hydroxypropionic acid and/or an ester thereof at the beginning of the dehydration step.

A catalyst used in the dehydration step, i.e., a dehydration catalyst is not particularly limited as long as it can convert hydroxypropionic acid to acrylic acid.

Examples of the catalyst include: crystalline metallosilicates such as zeolite; crystalline metalosilicates on which alkali metals, alkaline earth metals, transition metals or the like are supported by the method such as ion exchange; natural or synthetic clay compounds such as kaolinite, bentonite, montmorillonite; catalysts in which sulfuric acid, heteropoly acid, phosphoric acid or phosphate (e.g. alkali metal salts and alkaline earth metal salts of phosphoric acid, manganese phosphate, and zirconium phosphate), an alkali metal, or an alkaline earth metal is supported on a carrier such as alumina and silica; inorganic oxides or inorganic complex oxides such as $Al_2O_3$, $SiO_2$, $TiO_2$, $ZrO_2$, $SnO_2$, $V2O_5$, $SiO_2$—$Al_2O_3$, $SiO_2$—$TiO_2$, $SiO_2$—$ZrO_2$, $TiO_2$—$WO_3$, and $TiO_2$—$ZrO_2$; solid acid substances such as metal sulfates and metal phosphates (e.g., $MgSO_4$, $Al_2(SO_4)_3$, $K_2SO_4$, $AlPO_4$, and $Zr(SO_4)_2$); and solid basic substances such as calcium oxide, magnesium oxide, and hydrotalcite; and the like. Preferable catalysts are $Al_2O_3$, $SiO_2$, $SiO_2$—$Al_2O_3$, $TiO_2$, zeolite, zeolite on which an alkali metal or alkaline earth metal is supported, and catalysts in which phosphoric acid or phosphate, an alkali metal, and an alkaline earth metal is supported on a carrier.

The catalyst may be a catalyst molded body. The shape thereof is not particularly limited, and examples include such as spherical, cylinder, ring, and honeycomb shapes.

In terms of physical properties of the catalyst, from the standpoint of the catalytic activity and the like, the specific surface area determined by the BET method is preferably 0.01 to 300 $m^2/g$ and more preferably 0.1 to 400 $m^2/g$. The Hammett acidity function $H_0$ is preferably +4 to −10 and more preferably +2 to −8 from the standpoint of the catalytic activity, acrylic acid selectivity in product materials, catalyst life, and the like. The size of the catalyst is preferably 0.1 to 50 mm and more preferably 0.5 to 40 mm in length from the standpoint of the catalytic activity and pressure drop of the reactor.

The temperature of the catalyst layer is preferably maintained at 150 to 500° C. The temperature is maintained more preferably at 200 to 450° C., still more preferably at 220 to 430° C., and particularly preferably at 250 to 400° C. With this temperature range (150 to 500° C.), the reaction speed is fast, a side reaction is less likely to occur, and the acrylic acid yield is increased.

The reaction pressure is not particularly limited, and may be determined in consideration of the evaporation method of the raw material composition, productivity of the dehydration reaction, collection efficiency after the dehydration reaction, and the like. The reaction pressure is preferably 10 to 1000 kPa, more preferably 30 to 300 kPa, and still more preferably 50 to 250 kPa.

The dehydration reaction of hydroxypropionic acid is maintained stably by the above evaporation step and dehydration step. Still, carbonaceous substances may be gradually attached to the inside of the evaporator and reactor, and to the catalyst. In such a case, evaporation efficiency may be problematically lowered due to a blockage in the evaporator, reactor, and pipes and to lowered heat transfer efficiency of the evaporator. Moreover, productivity and selectivity may be lowered due to lowered catalytic activity, and the like. Removal of the formed carbonaceous substances can turn the reaction back to normal.

The carbonaceous substances on the dehydration catalyst may be removed by contact of the dehydration catalyst with an oxidant, thereby regenerating the catalyst.

The word "oxidant" in the present invention refers to compound of oxidative decomposing carbonaceous substances to carbon dioxide, carbon monoxide, and other carbon-containing compounds by the effect of oxidant.

The above regeneration method is used in the catalyst regeneration step in the method that includes a first hydroxypropionic acid reaction step having the steps of (a) evaporating a raw material composition and (b) dehydrating the evaporated raw material composition by contact with a dehydration catalyst, catalyst regeneration step for removing carbonaceous substances on the dehydration catalyst, and a second hydroxypropionic acid reaction, step having the step (a) and the step (b) in which the dehydration catalyst regenerated in the catalyst regeneration step is used.

The catalyst to be regenerated in the present invention is a catalyst used for dehydrating hydroxypropionic acid. On the catalyst, carbonaceous substances generated during the reaction of a vapor-phase contact with hydroxypropionic acid are deposited. The carbonaceous substances may be attached to any parts of the catalyst such as the catalyst surface and inside the pores.

As the oxidant, a liquid oxidant in which aqueous hydrogen peroxide, organic peroxide, nitric acid, nitrous acid, or the like is dissolved may be used, or gaseous oxidant may be used. Preferred is a gaseous oxidant.

The gaseous oxidant is gaseous molecules capable of providing carbonaceous substances with oxygen elements for oxidative decomposition of the carbonaceous substances. Examples thereof include such as oxygen (oxygen in the atmosphere also corresponds to an oxidant), ozone, nitrogen monoxide, nitrogen dioxide, and dinitrogen monoxide. At least one gaseous oxidant among these oxidants needs to be contained. For example, a mixed gas containing air and oxygen, a mixed gas containing nitrogen monoxide and oxygen may be used. Further, a mixed gas containing an oxidant and at least one inert gas randomly selected from nitrogen, carbon dioxide, argon, helium, and water vapor may be used.

In catalyst regeneration, the catalyst taken out from the reactor used in the first hydroxypropionic acid reaction may be exposed to an oxidant gas. In the present invention, however, a gaseous oxidant is preferably introduced into the reactor filled with a dehydration catalyst used in the step (b) for removal of the carbonaceous substances for facilitating regeneration of the catalyst.

Though a higher heating temperature of the catalyst in the catalyst regeneration leads to a shorter catalyst regeneration time, too high a temperature may cause reduction in the catalytic activity and selectivity due to a structural change in the catalyst. Commonly, the temperature is in a range of preferably 300 to 800° C., more preferably 320 to 700° C., and still more preferably 350 to 500° C. With a temperature of higher than 800° C., the physical structure and chemical properties of the catalyst may change (e.g., reduction in the catalyst surface area caused by sintering and crystal structural change of the catalyst caused by phase transition), lowering the catalytic activity and selectivity. The upper limit of the temperature depends on the catalyst species. In the case where the catalyst is calcined in preparation thereof, the heating temperature is preferably not higher than the calcining temperature.

For control of the heating temperature, the preset temperature of a heater used for heating the catalyst, oxidant concentration, and gas flow rate may be adjusted. In this case, the higher the preset temperature of a heater and/or oxidant concentration is, the higher the catalyst heating temperature is. While measuring the catalyst heating temperature continuously, the preset temperature of a heater and/or oxidant concentration can be adjusted for controlling the catalyst heating temperature. The method for controlling the catalyst heating temperature disclosed in JP-A 05-192590 may also be employed.

The oxidant concentration is preferably 1 to 21% by volume from the standpoint of temperature control, production cost, and the like.

The treatment time is preferably 1 to 100 hours and more preferably 2 to 50 hours from the standpoint of productivity of acrylic acid.

Figure 2:
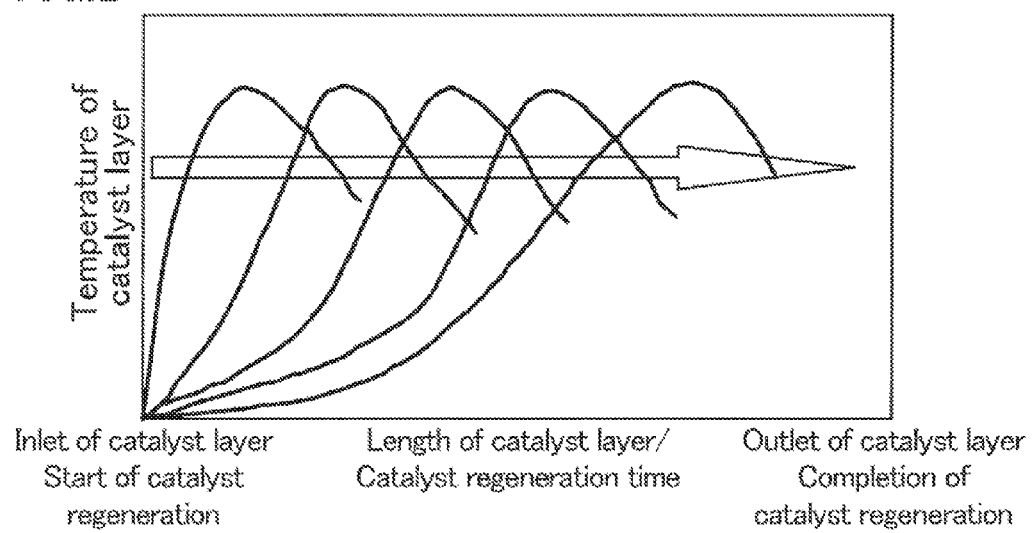
FIG. 2 is a view for showing a temperature change in a catalyst during oxidative decomposition for removing carbonaceous substances on the catalyst in a fixed bed-type continuous reactor.

The temperature change in the fixed bed continuous reactor is described with reference to FIG. 2. FIG. 2 is a schematic thermograph for showing a temperature change in the catalyst during removal of carbonaceous substances on the catalyst by oxidative decomposition. The catalyst layer temperature is plotted on the vertical axis. The catalyst regeneration time and the length of the catalyst layer in the fixed bed continuous reactor are plotted on the horizontal axis. The arrow indicates the gas flow direction in the fixed bed continuous reactor. As shown in the graph, the highest catalyst heating temperature (peak temperature) in the fixed bed continuous reactor is shifted over time from the inlet side to the outlet side (gas flow direction) of the fixed bed continuous reactor. That is, at the beginning of the oxidative decomposition for removing the carbonaceous substances, most of the oxidant is consumed in oxidative decomposition of the carbonaceous substances in the vicinity of the inlet side of the fixed bed continuous reactor. The position of this consumption is shifted to the outlet side over regeneration time. As shown in FIG. 2, it is a preferable mode of the present embodiment where the position of the peak temperature in the fixed bed continuous reactor is continuously shifted in the gas flow direction in the reactor for heating the catalyst at a temperature not higher than the calcining temperature in preparation of the catalyst.

In the method according to the present embodiment where the carbonaceous substances are removed by oxidative decomposition, catalytic components may be dispersed during the oxidative decomposition of the carbonaceous substances, though it depends on the type of the catalyst. In such a case, catalytic components are additionally supplied to achieve the required catalytic activity. Examples of the catalyst to be additionally supplied in such manner include a catalyst supporting a phosphorous compound. The catalyst supporting a phosphorous compound which has a phosphorous compound supported on a carrier such as silica and alumina is regenerated by supplementation of a catalytic component (phosphorous) dispersed in the dehydration step of hydroxypropionic acid and the oxidative decomposition for removal of the carbonaceous substances.

For supplementation of the catalytic component, the method for loading the catalytic component in preparation of the catalyst may be conducted again. Examples of the method include (1) supplementing a predetermined amount of a catalytic component to a catalyst taken out from a reaction tube by impregnation or the like, and (2) supplementing a catalytic component to a catalyst filled in the reaction tube contacted with a volatile compound (a compound containing phosphorous element such as phosphate ester) by a method disclosed in JP-A 02-290255, or the like.

The catalyst is regenerated by the above method. In order not to stop the dehydration of hydroxypropionic acid during the regeneration, plural reactors arranged in parallel may be used in such a manner that, while catalyst regeneration is performed in one reactor, dehydration of hydroxypropionic acid is performed in another reactor. Specifically, plural reactors are preferably used and, while the catalyst regeneration step is conducted in one reactor, the first or second hydroxypropionic acid reaction step is conducted in another reactor.

In the case of using plural reactors, the number of reactors needed corresponds to the time (reaction time) for producing acrylic acid by dehydration of hydroxypropionic acid and the time (regeneration time) for regenerating the catalyst by removing carbonaceous substances accumulated on the catalyst. If the regeneration time is shorter than the reaction time, the number of reactors used for dehydration of hydroxypropionic acid is one and the number of reactors used for catalyst regeneration is one. If the regeneration time is twice or less as long as the reaction time, the number of reactors used for dehydration of hydroxypropionic acid is one and the number of reactors used for catalyst regeneration is two. Accordingly, reduction in the number of the reactors used for catalyst regeneration leads to economical dehydration of hydroxypropionic acid. To reduce the number of reactors, the regeneration time is preferably as short as possible. Regeneration at a temperature as high as possible within a range not exceeding the upper limit of the catalyst regeneration temperature or the preset temperature of the reactor shortens the regeneration time. For the sake of this, the oxidant concentration, flow rate of a gaseous component introduced together with the oxidant, and the like may be controlled.

In the present invention, carbonaceous substances on the dehydration catalyst for hydroxypropionic acid are removed by contact with an oxidant. However, as mentioned above, hydroxypropionic acid tends to be converted to oligomers such as dimers and trimers. Especially in an evaporator for supplying a gaseous raw material to a reactor, since hydroxypropionic acid as the raw material is heated in the liquid form, conversion to oligomers easily occurs and the oligomers partially fail to be evaporated and remain in the evaporator, which may result in conversion to carbonaceous substances by heating for a long time. In such a case, a blockage in lines and deposition of the carbonaceous substances lowers the heat transfer coefficient.

In this case, the evaporator and pipes may be periodically cleaned or exchanged. Alternatively, carbonaceous substances remaining in the evaporator and pipes may also be removed by contact with an oxidant. The removal may be conducted by a method similar to the method for catalyst regeneration. Removal of carbonaceous substances in the evaporator and catalyst regeneration may be conducted separately or at once. Since the evaporator is connected with the reactor, removal of carbonaceous substances in the evaporator and catalyst regeneration may be conducted at once for efficiency. When an oxidant is supplied from the upstream side of the evaporator, carbonaceous substances in the evaporator are first removed and then the catalyst in the reactor is regenerated. Alternatively, an oxidant may be supplied to the evaporator and the reactor from each inlet side separately.

As a result, since carbonaceous substances in both the evaporator and the reactor are removed periodically, acrylic acid can be produced stably for a long time.

In the present invention, since the total amount of hydroxypropionic acid and/or an ester thereof supplied in the step (b) is controlled to 70% by mass or more, the reduction rate of the catalytic activity in the long-term reaction is smaller and the recovery rate of the catalytic activity by the catalyst regeneration is better than those of the case in which the total amount is not controlled.

In the present invention, the method for obtaining a composition containing acrylic acid by cooling a reaction product obtained from the exit of the reactor is not particularly limited. For example, the composition may be obtained by introducing a reaction product gas into a heat exchanger and concentrating the composition at a temperature lower than the dew point of the reaction product gas. For another example, the composition is obtained by bringing a reaction product gas into contact with an absorbent such as a solvent to absorb and cool the composition.

The acrylic acid concentration in the composition is preferably 5 to 95% by mass, more preferably 10 to 95% by mass, and still more preferably 20 to 95% by mass.

The composition of the thus-obtained reaction product contains water and acrylic acid which are main reaction products, and may also contain byproducts and the solvent and impurities in the raw material composition. In the case where the solvent is water, the composition in the form of an acrylic acid aqueous solution may be used as a raw material for polymers production. Alternatively, the composition may be purified to produce highly-pure acrylic acid.

The purification may be conducted by a known technique such as distillation, extraction, membrane separation, and crystallization. These techniques may be used in combination.

As mentioned above, purification of the acrylic acid composition obtained in the present invention provides highly pure acrylic acid. Accordingly, the method of the present invention also provides a method for producing highly pure acrylic acid.

The method specifically includes a step of purifying acrylic acid and/or an ester thereof by crystallization.

The following is a method in which the gaseous reaction product is liquidized by cooling condensation, solvent entrapment, or the like, water and the entrapped solvent contained in the obtained liquid are optionally removed by a conventionally known method (e.g., distillation), and the resulting liquid is crystallized to produce highly pure acrylic acid.

Here, crude acrylic acid refers to a composition containing acrylic acid resulting from the cooling step, and an acrylic acid aqueous solution is suitable.

The crystallization step may be conducted by a conventionally known method for separating propionic acid from crude acrylic acid, for example, by methods disclosed in JP-A 09-227445, JP-T 2002-519402, or the like.

In the crystallization step, crude acrylic acid is supplied to a crystallization device and crystallized to produce purified acrylic acid. The crystallization may be conducted by a conventionally known crystallization method and is not particularly limited. The crystallization can be performed using, for example, a continuous or batch crystallization device in one or two or more stages. The resulting crystalline acrylic acid is optionally further purified by washing, sweating, or the like, to produce purified acrylic acid with a higher purity.

Examples of the continuous crystallization device include a crystallization device in which a crystallization section, a solid-liquid separation section, and a crystal purification section are integrally formed (e.g., BMC (Backmixing Column Crystallizer) from Nippon Steel Chemical Co. Ltd, and Continuous Melting and Purifying Equipment from Tsukishima Kikai Co., Ltd.) and a crystallization device in which a crystallization section (e.g., CDC (Cooling Disk Crystallizer) from GMF GOUDA), a solid-liquid separation section (e.g., centrifuge and belt filter), and a crystal purification section (e.g., KCP (Kureha Crystal Purifier) purification device from Kureha Techno Engineering Co., Ltd.) are combined.

Examples of the batch crystallization device include a layered crystallization device (dynamic crystallization device) from Sulzer Chemtech and a static crystallization device from BEFS PROKEM.

In dynamic crystallization, crystallization is performed using a dynamic crystallization device. The dynamic crystallization device includes; a tubular crystallizer with a temperature control mechanism for crystallization, sweating, and melting; a tank for recovering mother liquor after sweating; and a circulation pump for supplying crude acrylic acid to the crystallizer. The dynamic crystallization device is capable of transferring crude acrylic acid from a reservoir provided at the lower part of the crystallizer, to an upper part of the tubular crystallizer by a circulation pump.

In static crystallization, crystallization is performed using a static crystallization device including: a crystallizer that is a tubular crystallizer with a temperature control mechanism for crystallization, sweating, and melting and has an outlet valve at a lower part; and a tank for recovering mother liquor after sweating.

Specifically, crude acrylic acid is introduced into a crystallizer as a liquid phase and acrylic acid in the liquid phase is coagulated on a cooling surface (tube wall surface). When the mass of the solid phase formed on the cooling surface reaches preferably 10 to 90% by mass and more preferably 20 to 80% by mass based on the mass of the crude acrylic acid introduced into the crystallizer, the liquid phase is promptly discharged from the crystallizer for separation of the solid phase and the liquid phase. The liquid phase may be pumped out (dynamic crystallization) or flowed out from the crystallizer (static crystallization). On the other hand, the solid phase taken out from the crystallizer may be purified by washing, sweating, or the like for further increase in purity.

In the case where dynamic crystallization or static crystallization is performed in several stages, the counter-current principle may be employed for advantageous crystallization. The acrylic acid crystallized in each stage is separated from the residual mother liquor and supplied in a stage for producing acrylic acid having higher purity. On the other hand, the residual mother liquor is supplied in a stage for producing acrylic acid having lower purity.

Additionally, in dynamic crystallization, lower purity of acrylic acid leads to difficulty in crystallization. In contrast, in static crystallization, since the residual mother liquor is in contact with the cooling surface for a longer time and the temperature is more likely to influence compared to the case of dynamic crystallization, crystallization is performed easily even when the purity of acrylic acid is lowered. Accordingly, to increase the recovery rate of acrylic acid, the mother liquor that eventually remains in dynamic crystallization may be subjected to static crystallization for further crystallization.

The number of stages required for crystallization depends on the level of desired purity. For obtaining highly pure acrylic acid, the number of stages required for the purification stage (dynamic crystallization) is commonly 1 to 6, preferably 2 to 5, and more preferably 2 to 4, and the number of stages required for the stripping stage (dynamic crystallization and/or static crystallization) is commonly 0 to 5 and preferably 0 to 3. Commonly, any stages where acrylic acid having a higher purity than crude acrylic acid supplied are included in purification stages, and the other stages are included in the stripping stages. The stripping stage is performed for recovering acrylic acid contained in the residual mother liquor from the purification stages. The stripping stage is not necessarily provided, and may be omitted when, for example, a distillation tower is used for separating low boiling components from the residual mother liquor in the crystallization device.

In any of dynamic crystallization and static crystallization cases, acrylic acid crystals obtained in the crystallization step may be treated as a commercial product as it is, or may be optionally further purified by washing, sweating, or the like to be treated as a commercial product. On the other hand, the residual mother liquor exhausted in the crystallization step may be discharged outside the system.

By the above methods, acrylic acid can be produced. The thus produced acrylic acid is, as already known, usable as a synthetic raw material of acrylic acid derivatives such as acrylic acid esters and hydrophilic resins such as polyacrylic acid and sodium polyacryrate. Obviously, the method for producing acrylic acid of the present invention can be incorporated in the methods for producing acrylic acid derivatives and hydrophilic resins.

In the method of the present invention, similarly to the production of acrylic acid by dehydration of hydroxypropionic acid, an acrylic acid ester can be efficiently produced by dehydration of a hydroxypropionic acid ester.

A hydroxypropionic acid ester is synthesized by esterification of hydroxypropionic acid using alcohol.

The alcohol used is not particularly limited and may be selected in accordance with applications. The alcohol has a carbon number of preferably 1 to 20, more preferably 1 to 10, and still more preferably 1 to 5.

Esterification is performed by heating hydroxypropionic acid and alcohol in the presence or absence of an esterification catalyst. Since hydroxypropionic acid is carboxylic acid, esterification proceeds even in the absence of a catalyst. However, from the standpoint of production efficiency, an esterification catalyst is preferably used.

A known esterification catalyst may be used, and examples thereof include: mineral acids such as hydrochloric acid, sulfuric acid, nitric acid, and phosphoric acid; solid acids such as zeolite and ion-exchange resin; inorganic acids such as heteropoly acid; sulfonic acids such as p-toluenesulfonic acid; and metallic compounds such as dibutyltin dilaurate, tin oxide, dibutyltin oxide, zinc acetate, and tetraalkoxy titanium.

The reaction temperature is preferably 50 to 300° C. and more preferably 80 to 250° C.

Since esterification is an equilibrium reaction, reactive distillation and a reaction with extraction of product materials are effective for yield increase.

In addition, a hydroxypropionic acid ester can be synthesized from hydroxypropionic acid and alcohol using microorganisms.

A hydroxypropionic acid ester having passed through the above steps is formed into an acrylic acid ester.

The thus obtained reaction products include an acrylic acid ester and water which are major reaction products and may also include acrylic acid, byproducts, and a solvent and impurities in the raw material composition. In such a case, a purification step is added for production of a highly pure acrylic acid ester. The purification is performed by a known technique such as distillation, extraction, membrane separation, and crystallization. These techniques may be used in combination.

<Production Method of a Hydrophilic Resin>

In the method for producing a hydrophilic resin according to the present invention, the acrylic acid and/or an ester thereof are produced by the above method and the monomer component including the acrylic acid and/or an ester thereof is polymerized. Specifically, acrylic acid and/or an ester thereof produced by the production method of the present invention is usable as a raw material of a hydrophilic resin such as water-absorbent resins and water-soluble resins.

In the case where the acrylic acid produced by the production method of the present invention is used as a raw material for producing a hydrophilic resin such as water-absorbent resins and water soluble resins, the polymerization reaction is likely to be controlled, so that the quality of the resulting hydrophilic resin is stable and various performances such as water absorption ability and dispersibility of inorganic materials are improved.

The hydrophilic resin is preferably a water-absorbent resin.

In production of a water-absorbent resin, for example, the acrylic acid and/or its salt (salt obtained by partially neutralizing the acrylic acid) obtained by the production method of the present invention is used as a main component (in an amount of preferably 70 mol % or more and still more preferably 90 mol % or more) of a monomer component. Further, about 0.001 to 5 mol % (relative to the amount of acrylic acid) of a crosslinking agent and about 0.001 to 2 mol % (relative to the amount of the monomer components) of a radical polymerization initiator are used in crosslinking polymerization thereof. The resulting product is then dried and crushed to give a water-absorbent resin.

The water-absorbent resin herein refers to a water-swellable and water-insoluble polyacrylic acid having a crosslinked structure, which forms a water-insoluble hydrogel containing preferably 25% by mass or less and more preferably 10% by mass or less of water soluble substances (water-soluble part) by absorbing pore water or saline in an amount of three times or more and preferably 10 to 1000 times the self-weight.

Specific examples of such a water-absorbent resin and a method for measuring the physical properties are disclosed, for example, in U.S. Pat. Nos. 6,107,358, 6,174,978, and 6,241,928.

The preferable method in terms of improvement in productivity is disclosed, for example, in U.S. Pat. Nos. 6,867,269, 6,906,159, 7,091,253, WO 2001/038402, and WO 2006/034806.

The following describes a series of steps for producing a water-absorbent resin by neutralization, polymerization, drying, and the like using an acrylic acid as a starting material.

The acrylic acid obtained by the production method of the present invention is partially supplied in a production process of a water-absorbent resin via a line. In the production process of an absorbent resin, acrylic acid is processed in the steps of neutralization, polymerization, and drying and subjected to a desired treatment so that a water-absorbent resin is produced. A desired treatment may be performed for improving various physical properties. For example, a crosslinking step may be conducted during or after polymerization.

The neutralization step is an optional step, and an exemplary method for neutralization includes mixing a predetermined amount of a basic substance in the form of powder or an aqueous solution with acrylic acid or polyacrylic acid (salt). It is to be noted that any conventionally known method may be employed and the method is not particularly limited.

The neutralization may be performed before or after polymerization, or before and after polymerization.

Examples of the basic substance used for neutralization of acrylic acid and polyacrylic acid (salt) include conventionally known basic substances such as (hydrogen) carbonates, alkali metal hydroxides, ammonia, and organic amines.

The neutralization rate of polyacrylic acid is not particularly limited and may be adjusted within an any neutralization rate (e.g., any value in a range of 30 to 100 mol %).

The polymerization method, used in the polymerization step is not particularly limited, and a conventionally known method such as polymerization by a radical polymerization initiator, radiation induced polymerization, polymerization by electron beam or active energy irradiation, and UV polymerization by a photosensitizer may be employed. A polymerization initiator to be used and various conditions such as polymerization conditions may be determined as appropriate. According to need, conventionally known additives may be used such as crosslinking agents, other monomers, water-soluble chain transfer agents, and hydrophilic polymers.

Acrylic acid salt polymers (i.e., water-absorbent resin) after polymerization are subjected to the drying step. The drying method is not particularly limited, and the drying step may be appropriately performed using a conventionally known dryer such as a hot air dryer, a fluidized-bed dryer, and a Nauta dryer at a desired drying temperature preferably at 70 to 230° C. The water-absorbent resin obtained through the drying step may be used as it is. Alternatively, the resin may be formed into a desired shape by granulating/crashing or surface-crosslinking before its use. Also, the resin may be subjected to post treatment in accordance with its application, such as addition of conventionally known additives (e.g., a reducing agent, a fragrant material, and a binder) before its use.

EXAMPLES

The present invention will be described in more detail by means of examples, but is not limited to these examples. The examples may be appropriately modified as long as the modification is not beyond the spirit of the above mentioned and mentioned later. Any of these modified examples are also within the scope of the present invention.

Hereinafter, unless otherwise specified, "%" indicates "% by mass" and "parts" indicates "parts by mass".

Preparation Example 1

Method for Obtaining a Composition Containing 3-Hydroxypropionic Acid (3HP)

*Klebsiella pneumoniae* ATCC25955 genomic DNA was used as a template. A region including a glycerol dehydratase gene (GD gene) and a glycerol dehydratase reactivation factor (GDR gene) was amplified by PCR using the following two primers. Amplified fragment terminals were cut with restriction enzymes NdeI and BglII, and the fragments were recovered by electrophoresis. The primers used for amplifying the GD gene and GDR gene sequences are designed based on the DNA sequences disclosed in GenBank Accession number: NC_009648.

```
Forward primer:                       (SEQ ID NO: 1)
5'-GCGCGCCATATGTTAATTCGCCTGACCGGCC-3'

Reverse primer:                       (SEQ ID NO: 2)
5'-GCGCGCAGATCTTCAGTTTCTCTCACTTAACG-3'
```

Vector sequences were amplified by the following two primers using a pACYCDuet-1 plasmid (TAKARA BIO INC.) as a template. A DNA fragment having NdeI site and BglII site behind a T7 promoter of the pACYCDuet-1 plasmid was amplified.

```
Forward primer:                    (SEQ ID NO: 3)
5'-GAAGGAGATATACATATGGCGCGC-3'

Reverse primer:                    (SEQ ID NO: 4)
5'-CCGATATCCAATTGAGATCTGCGCGC-3'
```

The amplified fragment was cut with restriction enzymes BglII and NdeI. The fragments were separated by electrophoresis for recovery thereof. These two DMA fragments were ligated and incorporated into *Escherichia coli* TOP10 competent cell (product of Invitrogen), and cultured on a chloram phenicol-containing plate, thereby producing chloram phenicol-resistant *Escherichia coli*. A plasmid DNA was extracted from the chloram phenicol-resistant *Escherichia coli* and its molecular weight was determined using restriction enzymes. It is confirmed that the determination clarified target GD gene and GDR gene were inserted in the pACYC-Duet-1 plasmid. The constructed recombinant plasmid was named as GD-GDR/pACYCDuet-1 and used in the following experiments.

*Escherichia coli* K-12 W3110 genomic DNA was used as a template. Using the following two primers, a γ-glutamyl-γ-aminobutyraldehyde dehydrogenase gene (aldH gene) was amplified by PCR. Amplified fragment terminals were cut with restriction enzymes NdeI and BglII, and the fragments were recovered by electrophoresis. The following primers were designed based on the DNA sequences disclosed in GenBank Accession number: AB200319.

```
Forward primer:                    (SEQ ID NO: 5)
5'-GGGGGGCCATATGAATTTTCATCATCTGGCTTACTG-3'

Reverse primer:                    (SEQ ID NO: 6)
5'-CCCCAGATCTTCAGGCCTCCAGGCTTATCCAGATG-3'
```

Vector sequences were amplified by the following two primers using a pUC18 plasmid as a template. A DNA fragment having an NdeI site behind a lac promoter of the pUC18 plasmid and a BamHI site at a position of a termination codon of a lacZ gene was amplified.

```
Forward primer:                    (SEQ ID NO: 7)
5'-CCCCCCCATATGTGTTTCCTGTGTGAAATTGTTATCCGCTCACAAT
TCCACACAATATACGAGCC-3'

Reverse primer:                    (SEQ ID NO: 8)
5'-CCCCGGATCCTTAGTTAAGCCAGCCCCGACACCCGCCAACACC-3'
```

The amplified fragment was cut with restriction enzymes BamHI and NdeI. The fragments were separated by electrophoresis for recovery thereof. These two DNA fragments were ligated and incorporated into *Escherichia coli* TOP10 competent cell. After culture thereof on an ampicillin-containing plate, a plasmid was extracted from the resulting transformant and its molecular weight was determined using restriction enzymes. The determination clarified aldH was inserted in the pUC18 plasmid as intended. The constructed recombinant plasmid was named as aldH/pUC18 and used in the following experiments.

In accordance with the protocol of *Escherichia coli* BL21 (DE3) competent cell (product of Merck), the constructed GD-GDR/pACYCDuet-1 and aldH/pUC18 were incorporated by heat shock to form *E. coli* (SD-GDR/pACYCDuet-1, aldH/pUC18).

The *E. coli* (GD-GDR/pACYCDuet-1, aldH/pUC18) was shake-cultured in a LB liquid medium (5 mL) containing ampicillin (100 ppm) and chloram phenicol (50 ppm) (composition per liter of the LB medium; 10 g of tripton, 5 g of yeast extract, and 10 g of NaCl) at 37° C. for 16 hours to give a precultured fluid. Next, the precultured fluid (5 mL) was inoculated into a NS liquid medium (1 L) containing ampicillin (100 ppm) and chloram phenicol (50 ppm), and cultured at 37° C. with agitation at a rate of 725 rpm and aeration at a rate of 1 L/min. The NS liquid medium contains 40 g/L of glycerin, 10 g/L of ammonium sulfate, 2 g/L of potassium dihydrogen phosphate, 6 g/L of dipotassium hydrogen phosphate, 1 g/L of magnesium sulfate heptahydrate, and 40 g/L of a yeast extract. A jar fermenter from Biott, BMJ-02NP2, was used for culture and ammonia water was used to control the pH value of the culture fluid to 7 during the culture. At eight hours after culture initiation, a 1 M IPTG solution (1 mL) and 8 mM adenosylcobalamin solution (1 mL) were added. The culture was performed for 100 hours with, appropriate addition of glycerin to avoid depletion of the glycerin during the culture. The resulting culture fluid was centrifuged for recovery of the supernatant thereof.

Product materials in the supernatant of the culture fluid were analyzed by high performance liquid chromatography mentioned below. The peak of 3-hydroxypropionic acid as a product material, was found at a position of 7.9 minutes. The concentration of 3-hydroxypropionic acid in the culture fluid was 2% by mass.

<Analysis Conditions in High Performance Liquid Chromatography>

Used column: YMC-pACK FA

Flow rate: 1 mL/min

Injection amount: 10 mL

Eluent: methanol/acetonitrile/$H_2O$=40/5/55 (V/V/V)

Internal standard: 2-Hydroxy-2-methyl-n-butyric Acid

Detection: UV 400 nm

Internal standard fluid (200 μL) was added to the culture supernatant (100 μL). A reagent A (200 λL) and a reagent B (200 μL) of hydroxycarboxylic acid labeling reagents (YMC Co., Ltd.) were further added, and mixed thoroughly. The mixture was treated at 60° C. for 20 minutes. A reagent C (200 μL) of hydroxycarboxylic acid labeling reagents (YMC Co., Ltd.) was added thereto and mixed well. After treatment at 60° C. for 15 minutes, the resulting fluid was cooled to ambient temperature and filtered through a 0.45-mm. filter, thereby preparing an LC analytic sample.

A 2 wt % 3-hydroxypropionic acid-containing culture fluid (30 g) from which microorganisms are removed, tridecylamine (180 g), and dodecanol (20 g) were added into a 500-mL three neck flask. The flask was submerged in an oil bath and connected to a vacuum pump. The flask was heated while the solution therein was stirred. When the solution temperature reached 85° C., the vacuum pump was turned on. During the reaction, ammonium 3-hydroxypropionate was decomposed to discharge ammonia and water. These are removed by a cold trap under reduced pressure. At the same time, 3-hydroxypropionic acid produced by decomposition of ammonium 3-hydroxypropionate was extracted into an organic phase formed of tridecylamine and dodecanol. To the organic phase formed of tridecylamine and dodecanol which contains 3-hydroxypropionic acid, a ⅕ volume of water was added and mixed. The mixture was heated to 140° C. to give an aqueous solution containing 3-hydroxypropionic acid.

Example 1

The above 3-hydroxypropionic acid (3HP) was adjusted to a 12% by mass aqueous solution as a raw material composition.

A stainless-steel reaction tube having an inner diameter of 10 mm was filled with stainless-steel 1.5-mm Dixon Packing as an evaporation layer (surface area of 37 $cm^2/cm3$). The reaction tube was heated to 300° C. in an electric furnace, and the raw material composition was supplied to the upper part of the reaction tube at a rate of 16.8 g/hour. At the same time, nitrogen gas was introduced at a rate of 3 L/hour, and the SV at the evaporation layer part was controlled to 10000. The reaction gas flowed out from the lower part of the reaction tube was cooled to obtain collected liquid. The collected liquid was analyzed by liquid chromatography and the conversion of 3HP was found to be 19% (3HP residual rate of 81%).

Subsequently, a commercially available γ-alumina pellet (Saint-Gobain K. K.) was put as a solid catalyst under the evaporation layer to form a stacking of the evaporation layer and a catalyst layer. The reaction tube was heated in an electric furnace at 300° C. The raw material was supplied to the upper part of the reaction tube at a rate of 16.8 g/hour. At the same time, nitrogen gas was introduced at a rate of 3 L/hour. The reaction was thus continued for eight hours.

The reaction gas flowed out from the lower part of the reaction tube was cooled to be collected, giving a reaction liquid. The inlet pressure of the reaction tube was constant during the reaction. An analysis of the resulting reaction liquid by liquid chromatography clarified that the conversion of 3HP was 95%, and the acrylic acid yield was 93 mol % (here and hereinafter, the conversion and yield were determined based on the standard of the amount of the raw material added in the step (a)). No accretion was found on the packing and catalyst removed after the reaction.

Example 2

The reaction was carried out in the same manner as in Example 1, except that the packing as the evaporation layer was changed to quarts glass wool (surface area of 537 $cm^2/cm^3$), the rate of supplying the raw material was changed to 34.4 g/hour, the rate of introducing nitrogen gas was changed to 6 L/hour, and the SV at the evaporation layer part was controlled to 20000.

The inlet pressure of the reaction tube was constant during the reaction. The conversion of 3HP in the case of the reaction only with the packing was 4% (3HP residual rate of 96%). The conversion of 3HP in the case of the reaction with a stacking of the packing and the catalyst was 92% and the acrylic acid yield was 91 mol %. No accretion was found on the packing and catalyst removed after the reaction.

Comparative Example 1

The reaction was carried out in the same manner as in Example 1, except that the packing as the evaporation layer was changed to glass beads with a diameter of 2 mm (surface area of 19 $cm^2/cm^3$). The SV at the evaporation layer part was 10000.

The conversion of 3HP in the case of the reaction only with the packing was 51% (3HP residual rate of 49%). In the case of the reaction with a stacking of the packing and the catalyst, the inlet pressure of the reaction tube rose in three hours from the reaction start to cause a blockage in the reaction tube, and the reaction was stopped. A large amount of a dark accretion was found on the packing and the catalyst removed after the reaction.

Comparative Example 2

The reaction was carried out in the same manner as in Example 1, except that the packing as the evaporation layer was changed to a stainless-steel ball with a diameter of 3 mm (surface area of 11 $cm^2/cm^3$). The SV at the evaporation layer part was 10000.

The conversion of 3HP in the case of the reaction only with the packing was 35% (3HP residual rate of 65%). In the case of the reaction with a stacking of the packing and the catalyst, the inlet pressure of the reaction tube rose in five hours from the reaction start to cause a blockage in the reaction tube, and the reaction was stopped. The packing removed after the reaction was covered with black carbonaceous substances and a dark accretion was found on the removed catalyst.

Comparative Example 3

The packing as the evaporation layer of Example 1 was removed and the liquid raw material composition was directly supplied onto the catalyst for the reaction. The inlet pressure of the reaction tube rose in an hour from the reaction start to cause a blockage in the reaction tube, and the reaction was stopped. The large amount of a dark accretion was found on the catalyst removed after the reaction.

Example 3

A stainless-steel tube with an inner diameter of 10 mm was filled with stainless-steel Dixon packing (1.5 mm) as an evaporation layer and arranged in an electric furnace, thereby preparing an evaporator. Another stainless-steel tube with an inner diameter of 10 mm was filled with silica alumina (JGC Corporation) as the catalyst and arranged in an electric furnace, thereby preparing a reactor. The outlet of the evaporator was connected to the inlet of the reactor by a stainless-steel tube, and an electric heater was set to heat them.

The temperature inside the evaporator was set to 275° C. The same raw material composition as used in Example 1 was supplied from the upper part of the evaporator at a rate of 33.5 g/hour. At the same time, nitrogen gas was introduced at a rate of 6 L/hour and the SV inside the evaporator was controlled to 2000. Outlet gas from the evaporator was cooled to be collected, and the resulting liquid was analyzed. Table 1 shows the results.

The temperature inside the evaporator was set to 275° C. and the temperature inside the reactor was set to 300° C. The same raw material composition as used in Example 1 was supplied from the upper part of the evaporator at a rate of 33.5 g/hour. At the same time, nitrogen gas was introduced at a rate of 6 L/hour. Outlet gas from the evaporator was directly supplied to the reactor and the reaction was carried out continuously for eight hours. Outlet gas from the reactor was cooled to be collected, and the resulting liquid was analyzed. Table 1 shows the results.

Since the outlet gas from the evaporator was directly supplied to the reactor, the 3HP conversion analyzed of the outlet gas from the evaporator was the same as the 3HP conversion of the gas supplied to the inlet of the reactor.

In Tables 1 to 2 below, the 3HP conversion, AA yield, and AA selectivity were the reaction results (average determined by sampling the reaction liquid) in the reaction time for eight hours.

In Tables 1 to 2 below, the total amount of hydroxypropionic acid and/or an ester thereof supplied to the inlet of the reactor was determined by the formula [100-(3HP conversion at the cutlet of the evaporator) ] (%).

Example 6

The experiment was carried out in the same manner as in Example 4, except that the temperature inside the evaporator was changed to 330° C. Table 1 shows the results.

Comparative Example 5

The experiment was carried out in the same manner as in Comparative Example 4, except that the temperature inside the evaporator was changed to 330° C. Table 1 shows the results.

TABLE 1

|  | Example 3 | | Example 4 | | Comparative Example 4 | |
| --- | --- | --- | --- | --- | --- | --- |
| SV inside the evaporator (/hour) | 2000 | | 1000 | | 500 | |
| Temperature inside the evaporator (° C.) | 275 | | 275 | | 275 | |
| Temperature inside the reactor (° C.) | 300 | | 300 | | 300 | |
|  | Outlet of the evaporator | Outlet of the reactor | Outlet of the evaporator | Outlet of the reactor | Outlet of the evaporator | Outlet of the reactor |
| 3HP conversion | 14% | 100% | 20% | 100% | 37% | 100% |
| AA yield | 12% | 98% | 17% | 95% | 30% | 89% |
| AA selectivity | 86% | 96% | 85% | 95% | 81% | 89% |
|  | Example 5 | | Example 6 | | Comparative Example 5 | |
| SV inside the evaporator (/hour) | 2000 | | 1000 | | 500 | |
| Temperature inside the evaporator (° C.) | 330 | | 330 | | 330 | |
| Temperature inside the reactor (° C.) | 300 | | 300 | | 300 | |
|  | Outlet of the evaporator | Outlet of the reactor | Outlet of the evaporator | Outlet of the reactor | Outlet of the evaporator | Outlet of the reactor |
| 3HP conversion | 17% | 100% | 29% | 100% | 47% | 100% |
| AA yield | 15% | 98% | 24% | 94% | 37% | 86% |
| AA selectivity | 88% | 96% | 83% | 94% | 79% | 86% |

In each table, "3HP" refers to 3-hydroxypropionic acid and "AA" refers to acrylic acid.

Example 4

The experiment was carried out in the same manner as in Example 3, except that the rate of supplying the raw material composition was changed to 16.7 g/hour, the rate of supplying nitrogen gas was changed to 3 L/hour, and the SV inside the evaporator was controlled to 1000. Table 1 shows the results.

Comparative Example 4

The experiment was carried out in the same manner as in Example 3, except that the rate of supplying the raw material composition was changed to 7.8 g/hour, and the rate of supplying nitrogen gas was changed to 1.5 L/hour. The SV inside the evaporator was 500. Table 1 shows the results.

Example 5

The experiment was carried out in the same manner as in Example 3, except that the temperature inside the evaporator was changed to 330° C. Table 1 shows the results.

Example 7

In a supply line for the raw material composition, a back pressure valve and a heater were arranged for heating the raw material composition to 200° C. in the liquid form before being supplied to the evaporator. The supply line for the raw material composition was set to have an outlet with an inner diameter of 1 mm and the raw material composition in a gas-liquid mixed state was supplied to the evaporator by spraying. Except for the above changes, the experiment was carried out in the same manner as in Example 4.

As a result of an analysis of a liquid collected from the outlet of the evaporator, the 3HP conversion in the evaporator was 17% (3HP residual rate of 83%).

As a result of an analysis of a liquid, collected from the outlet of the reactor, the 3HP conversion was 100% and the acrylic acid yield was 95 mol %.

Example 8

The reaction was carried out continuously for 50 hours under the same conditions as in Example 4. Favorably, the average of 3HP conversion was 95% and the average of acrylic acid yield was 91% in 50 hours. Without blockage in the evaporator or reactor, the reaction continued stably.

Example 9

Spherical ZSM-5 zeolite (proton-type) was synthesized in accordance with the method disclosed in JP-A 2009-190915.

The experiment was carried, out in the same manner as in Example 4, except that the temperature inside the evaporator was set to 250° C., nitrogen gas to be supplied was preliminary heated to 350° C., and the catalyst was changed to the ZSM-5. Gas from the outlet of the evaporator was cooled to be collected, As a result of an analysis of the obtained liquid by liquid chromatography, the 3HP conversion was 15% (3HP residual rate of 85%).

Subsequently, gas from the outlet of the evaporator was directly supplied to the reactor and the reaction was carried out continuously for eight hours. The outlet gas of the reactor was cooled to be collected. As a result of an analysis of the obtained liquid by liquid chromatography, the 3HP conversion was 100%, the acrylic acid yield was 97 mol %. No accretion was found on the packing and catalyst removed after the reaction.

Example 10

The 3HP solution prepared in Example 1 was condensed in a thin-film evaporator. Under the condition of a pressure of 20 mmHg (=2.68 kPa) and a jacket temperature of 50° C., low boiling fractions were removed and water was added to the resulting bottom liquid so that the 3HP concentration was set to 80% by mass.

The reaction was carried out in the same manner as in Example 1, except that the raw material composition having a 3HP concentration of 80% by mass was supplied at a rate of 2.5 g/hour, nitrogen was supplied at a rate of 22.2 L/hour, and the SV inside the evaporator was controlled to 11000. As a result of an analysis of the collected liquid having passed through only the evaporation layer, the 3HP conversion was 20% (3HP residual rate of 80%). As a result of an analysis of the collected liquid having passed through the evaporation layer and the catalyst layer, the 3HP conversion was 93% and the acrylic acid yield was 90 mol %.

Example 11

Calcium hydroxide was used instead of ammonia water in ph adjustment of a culture fluid of Preparation Example 1. After the culture, a sulfuric acid aqueous solution in an amount of 98 mol % based on the amount of calcium hydroxide used was dropwise-added to the culture fluid, and the resulting liquid was stirred at 30° C. for two hours. Microorganisms and formed calcium sulfate in the resulting liquid were removed by filtration. The filtrate was heated at 100 ° C. for 2 hours for deposition of protein degradation products. The deposit was removed by filtration. The filtrate was condensed in a thin-film evaporator. Under the conditions of a pressure of 20 mmHg (=2.66kPa) and a jacket temperature of 50° C., low boiling fractions were removed (first thin-film evaporation). The resulting bottom liquid was further evaporated in a thin-film evaporator. Under the conditions of a pressure of 2 mmHg (=0.266 kPa) and a jacket temperature of 100° C., fractions containing 3HP were obtained (second thin-film evaporation). Water was added to the resulting fractions such that the mass of 3HP was 12 % by mass, thereby preparing a 3HP solution. Phosphate ions, sulfate ions, ammonium ions, magnesium ions, and potassium ions in the solution were analyzed by ion chromatography. The total of these was 150 mass ppm (=0.015 % by mass) relative to the mass of 3HP.

A dehydration reaction was carried out under the same conditions as in Example 4 using the 3HP solution as a raw material composition. Table 2 shows the results.

Comparative Example 6

After addition of water to the bottom liquid resulting from the first thin-film evaporation, in Example 11, cation exchange resin Amberlyst 15 (product of ORGAPO CORPORATION) was added. Then ion components in the liquid were adsorbed by stirring at 30° C. for two hours. After removal of the cation-exchange resin and deposit, the liquid was prepared such that the mass of 3HP was 12% by mass, thereby preparing a 3HP solution. Phosphate ions, sulfate ions, ammonium ions, magnesium ions, and potassium ions in the solution were analyzed by ion. chromatography. The total of these was 1.1% by mass relative to the mass of 3HP.

A dehydration reaction was carried out under the same conditions as in Example 4 using the 3HP solution as a raw material composition. Table 2 shows the results.

TABLE 2

|  | Example 11 | Comparative Example 6 |
| --- | --- | --- |
| SV inside the evaporator (/hour) | 1000 | 1000 |
| Temperature inside the evaporator (° C.) | 275 | 275 |
| Temperature inside the reactor (° C.) | 300 | 300 |

|  | Outlet of the evaporator | Outlet of the reactor | Outlet of the evaporator | Outlet of the reactor |
| --- | --- | --- | --- | --- |
| 3HP conversion | 20% | 100% | 42% | 98% |
| AA yield | 17% | 95% | 24% | 74% |
| AA selectivity | 85% | 95% | 57% | 76% |

Example 12

(First Reaction Step of 3HP)

The spherical ZSM-5 zeolite (proton type) synthesized in Example 9 was put in the reactor of Example 1 as a catalyst, and the reaction was carried out in the same manner. The collected liquid from the outlet of the reactor was sampled hourly for tracking of a change in the reaction results over time. The reaction results in 1 to 2 hours after the reaction were a 3HP conversion of 100% and an acrylic acid yield of 95 mol %. The reaction results in 7 to 8 hours after the reaction was a 3 HP conversion of 95% and an acrylic acid yield of 91 mol %. Accordingly, reduction in the catalytic activity over time was observed. Dark coloring was observed in the Dixon packing and catalyst removed after the reaction.
(Regeneration of Catalyst)

The Dixon packing and catalyst removed from the reactor were thinly placed on a ceramic plate and placed in a calcining furnace. Then, air was introduced into the calcining furnace at a flow rate of 0.5 L/minutes and the temperature inside was raised to 500° C. over an hour. The temperature was maintained for an hour for oxidative decomposition of carbonaceous substances on the catalyst, thereby regenerating the catalyst. After cooling, the removed Dixon packing and catalyst respectively turned color to their original silver and white.
(Second Reaction Step of 3HP)

The catalyst obtained in the catalyst regeneration was again put in the reactor, and a dehydration reaction of 3HP was carried out under the same condition as in the first reaction.

The reaction results in 1 to 2 hours after the reaction start were a 3HP conversion of 100% and an acrylic acid yield of 94 mol %. The reaction results in 7 to 8 hours after the reaction start were a 3HP conversion of 96% and an acrylic acid yield of 92 mol %. The catalyst regeneration allowed the second reaction to have similar reaction results as in the first reaction.

The catalyst (sample 1-1) after the first reaction, the catalyst (sample 1-2) after the catalyst regeneration, and the catalyst (sample 1-3) after the second reaction were analyzed using a differential thermal/ thermo gravimetry analyzer. In analysis, the test sample (30 mg) was heated to 800° C. at a rate of 10° C./minute and the introduction rate of the air was 50 mL/minute. The analysis clarified that the weight reduction rate was 5.0% for the sample 1-1, 0.5% for the sample 1-2, and 5.1% for the sample 1-3. It indicates that the catalyst regeneration step reduced the carbonaceous substances to regenerate the catalytic activity.

Example 13

The reaction was carried out in the same manner as in Example 11, except that the dehydration catalyst was changed to γ-alumina pellet.
(First 3HP Reaction Step)

The reaction results in 1 to 2 hours after the reaction start were a 3HP conversion of 100% and an acrylic acid yield of 97 mol %. The reaction results in 7 to 8 hours after the reaction start were a 3HP conversion of 89% and an acrylic acid yield of 86 mol %. The reduction in the catalytic activity over time was observed.
(Catalyst Regeneration Step)

The catalyst regeneration was carried out with the catalyst being kept in the reactor. After the first reaction, the reactor was heated to 450° C. and nitrogen was introduced at a rate of 5 L/hour for an hour. Subsequently, an oxidant-containing gas (oxygen (2% by volume) and nitrogen (the rest)) was introduced at a rate of 1.5 L/hour. Then, a temperature increase in the catalyst layer was observed. Next, gas (oxygen (5% by volume) and nitrogen (the rest)) with a larger oxidant content was introduced, and gas (oxygen (8% by volume) and nitrogen (the rest)) with a still larger oxidant content was introduced for about 24 hours in which fever caused by oxidative decomposition of carbonaceous substances was receded.
(Second 3HP Reaction Step)

After the catalyst regeneration, a dehydration reaction of 3HP was continuously carried out under the same conditions as those in the first reaction. The reaction results in 1 to 2 hours after the reaction start were a 3HP conversion of 100% and an acrylic acid yield of 97 mol %. The reaction results in 7 to 8 hours after the reaction start were a 3HP conversion of 88% and an acrylic acid yield of 86 mol %. The catalyst regeneration allows the second reaction to have similar reaction, results as in the first reaction.

Example 14

The first 3HP reaction was carried out under the same reaction conditions as those in Example 4 except that the reaction time was prolonged to 50 hours. After the reaction, the catalyst regeneration was carried out in the same manner as in Example 13. Then, the second 3HP reaction was carried out for 50 hours. Table 3 shows the results.

Though the 3HP conversion was decreased over time in the first reaction step, the catalyst regeneration allowed the second reaction to have similar reaction results as in the first reaction.

Comparative Example 7

The first 3HP reaction was carried out under the same reaction conditions as those in Comparative Example 5 except that the reaction time was prolonged to 50 hours. After the reaction, the catalyst regeneration was carried out in the same manner as in Example 13. Then, the second 3HP reaction was carried out for 50 hours. Table 3 shows the results.

The 3HP conversion was decreased over time in the first reaction step, and the decreasing rate was faster than that in Example 14. In the second reaction step after the catalyst regeneration, the 3HP conversion was smaller than that in the first reaction, which indicated the catalyst was not completely regenerated.

TABLE 3

|  | Example 14 | | Comparative Example 7 | |
| --- | --- | --- | --- | --- |
|  | 3HP conversion | AA yield | 3HP conversion | AA yield |
| 1 hr | 100% | 96% | 100% | 88% |
| 25 hr | 96% | 92% | 94% | 80% |
| 50 hr | 93% | 90% | 89% | 76% |
| Catalyst regeneration | | | | |
| 1 hr | 100% | 96% | 96% | 84% |
| 25 hr | 95% | 92% | 90% | 77% |
| 50 hr | 92% | 90% | 85% | 72% |

In Table 3, the 3HP conversion and AA yield are the values measured at the outlet of the reactor. In terms of the change over time in Table 3, 1 hr, 25 hr, and 50 hr respectively show the reaction results in an hour of 0-1 hr, 24-25 hr, and 49-50 hr.

Example 15

Purification of Acrylic Acid by Crystallization

As a result of distillation of the aqueous solution of acrylic acid obtained in Example 1, crude acrylic acid containing 86.5% by mass of acrylic acid was obtained in a bottom of tower. The crude acrylic acid was used as mother liquor in crystallization. In the crystallization, the mother liquor was cooled to a temperature range of ambient temperature (about 15° C.) to −5.8° C. for crystallization, and after maintenance at that temperature, the crystals were separated from the liquid by suction filtration. The separated crystals were molten and partially sampled for analysis. The rest was used as mother liquor again in crystallization. In the crystallization, the mother liquor was cooled to a temperature range of ambient temperature (about 15° C.) to 4.8° C. for crystallization, and after maintenance at that temperature, the crystals were separated from the liquid by suction filtration. As a result of crystallization twice, purified acrylic acid was obtained. The acrylic acid purity was at least 99.9% by mass.

Example 16

Preparation Example of Water-Absorbent Resin

To the purified acrylic acid obtained in Example 15, 60 ppm by mass of a polymerization inhibitor was added. Next, to a NaOH aqueous solution obtained from caustic soda containing 0.2 ppm by mass of iron, the polymerization inhibitor-containing acrylic acid was added with cooling (liquid temperature of 35° C.) for 75 mol % neutralization. In the resulting sodium acrylate aqueous solution having a neutralization rate of 75 mol % and concentration of 35% by mass, 0.05 mol % (value based on the amount of the sodium acrylate aqueous solution) of polyethylene glycol diacrylate as an inner crosslinking agent was dissolved, thereby obtaining monomer components. An amount of 350 g of the monomer components was placed in a 1-L cylindrical container and nitrogen was introduced thereinto for deaeration at a rate of 2 L/min for 20 minutes. Next, an aqueous solution containing 0.12 g/mol (value based on the amount of the monomer components) of sodium persulfate and 0.005 g/mol (value based on the amount of the monomer components) of L-ascorbic acid was added with stirring by a stirrer for initiation of polymerization. After the polymerization started, stirring was stopped and static aqueous polymerization was carried out. The temperature of the monomer components reached the peak polymerization temperature of 108° C. in about 15 minutes (polymerization peak time), then the polymerization was continued, for 30 minutes. Polymers were taken out from the cylindrical container and aqueous gel crosslinked polymers were obtained.

The aqueous gel crosslinked polymers were fractionated at 45° C. with a meat chopper (pore diameter; 8 mm), and heated to be dried using a hot-air dryer at 170° C. for 20 minutes. The dried polymers (solids content: about 95%) was crushed with a roll mill to have a grain size of 600 to 300 μm classified by a JIS standard sieve, thereby producing a polyacrylic acid water-absorbent resin (neutralization rate; 75%).

The acrylic acid produced by the method for producing acrylic acid of the present invention had polymerizability equal to that of acrylic acid obtained by the method for producing acrylic acid using propylene as a raw material, and produced the water-absorbent resin having no odors and equal properties.

Accordingly, a blockage in a reaction tube and reduction in the catalytic activity are suppressed by employment of the method for producing acrylic acid and/or an ester thereof, the method including the steps of; (a) evaporating the raw material composition; and (b) dehydrating the evaporated raw material composition by contact with a dehydration catalyst, wherein the total amount of hydroxypropionic acid and/or an ester thereof supplied in the step (b) is controlled to be 70% by mass or more based on 100% by mass of the total amount of hydroxypropionic acid and/or an ester thereof supplied in the step (a). As a result, the hydroxypropionic acid and/or an ester thereof are efficiently converted, enabling continuous production of acrylic acid and/or an ester thereof stably in high yield for a long time. The mechanism of the above effect was presumably the same in every aspect.

Accordingly, the results of the examples indicate that the present invention is applicable and exerts an advantageous effect in the entire technical scope of the present invention and in the various embodiments disclosed herein.

INDUSTRIAL APPLICABILITY

The present invention enables continuous production of high-quality acrylic acid and/or an ester thereof stably in high yield for a long time using hydroxypropionic acid and/or an ester thereof as a raw material. Further, the present invention highly contributes to the efforts against global warming when a raw material obtained or prepared from renewable bio-based resources (e.g., biomass) was used.

EXPLANATION OF REFERENCES

1. Scale
2. Pump
3. Evaporator
4. Connecting pipe
5. Reactor
6. Thermometer

---

The invention claimed is:

1. A method for producing acrylic acid and/or an ester thereof from a raw material composition containing hydroxypropionic acid and/or an ester thereof, the method comprising the steps of:
   (a) evaporating the raw material composition; and
   (b) dehydrating the evaporated raw material composition by contact with a dehydration catalyst,
   wherein the total amount of hydroxypropionic acid and/or an ester thereof supplied in the step (b) is controlled to be 70% by mass or more based on 100% by mass of the total amount of hydroxypropionic acid and/or an ester thereof supplied in the step (a).

2. The production method according to claim 1, wherein at least part or all of the hydroxypropionic acid in the raw material composition is hydroxypropionic acid obtainable by fermentation.

3. The production method according to claim 1,
wherein an inorganic compound in the raw material composition is 1% by mass or less based on 100% by mass of the total amount of the hydroxypropionic acid and/or an ester thereof.

4. The production method according to claim 1, step (a) further comprises introducing water and/or an inert gas to the raw material composition, and
wherein the total amount of water and/or an inert gas supplied in the step (a) is 0.5 times by mole or more of the total amount of the hydroxypropionic acid and/or an ester thereof in the raw material composition.

5. The production method according to claim 1,
wherein the hydroxypropionic acid is 3-hydroxypropionic acid.

6. The production method according to claim 1,
wherein a carbonaceous substance formed on the dehydration catalyst in the step (b) is removed by contact with an oxidant.

7. The production method according to claim 6,
wherein the oxidant is a gaseous oxidant.

8. The production method according to claim 7,
wherein the carbonaceous substance is removed by introducing the gaseous oxidant into a reactor filled with the dehydration catalyst used in the step (b).

9. The production method according to claim 6,
wherein the method comprises:
a first hydroxypropionic acid reaction step including the step (a) and the step (b);
catalyst regeneration step for removing the carbonaceous substance on the dehydration catalyst; and
a second hydroxypropionic acid reaction step including the step (a) and the step (b) in which the dehydration catalyst regenerated in the catalyst regeneration step is used.

10. The production method according to claim 9,
wherein plural reactors are used in production of acrylic acid and/or an ester thereof, and,
while the catalyst regeneration step is performed in a first reactor, the first or second hydroxypropionic acid reaction step is performed in another reactor.

11. The production method according to claim 9,
wherein the method further includes a step of removing a carbonaceous substance formed in an evaporator in the step (a) by contact with an oxidant.

12. The production method according to claim 1,
wherein the method further includes a step of purifying acrylic acid and/or an ester thereof by crystallization.

13. A method for producing a hydrophilic resin comprising a step of
producing a monomer component containing an acrylic acid and/or an ester thereof from a raw material composition containing hydroxypropionic acid and/or an ester thereof, comprising the steps of:
(a) evaporating the raw material composition; and
(b) dehydrating the evaporated raw material composition by contact with a dehydration catalyst, wherein the total amount of hydroxypropionic acid and/or an ester thereof supplied in the step (b) is controlled to be 70% by mass or more based on 100% by mass of the total amount of hydroxypropionic acid and/or an ester thereof supplied in the step (a), and
polymerizing the monomer component containing the acrylic acid and/or an ester thereof.

14. The method for producing a hydrophilic resin according to claim 13,
wherein the hydrophilic resin is a water-absorbent resin.

* * * * *